United States Patent
Almagro et al.

(10) Patent No.: US 10,179,812 B2
(45) Date of Patent: Jan. 15, 2019

(54) METHOD OF TREATING IDIOPATHIC PULMONARY FIBROSIS BY ADMINISTERING HUMAN ONCOSTATIN M ANTIBODIES

(71) Applicant: Janssen Biotech, Inc., Horsham, PA (US)

(72) Inventors: Juan Carlos Almagro, Boston, MA (US); William DuBell, Jamison, PA (US); Johann Fransson, San Diego, CA (US); Jose Pardinas, Spring House, PA (US); Gopalan Raghunathan, San Diego, CA (US)

( * ) Notice: Subject to any disclaimer, the term of this patent is extended or adjusted under 35 U.S.C. 154(b) by 0 days.

(21) Appl. No.: 15/423,189

(22) Filed: Feb. 2, 2017

(65) Prior Publication Data

US 2017/0145090 A1 May 25, 2017

Related U.S. Application Data

(60) Division of application No. 14/870,774, filed on Sep. 30, 2015, now Pat. No. 9,587,018, which is a division of application No. 14/104,520, filed on Dec. 12, 2013, now Pat. No. 9,163,083, which is a continuation of application No. 13/269,976, filed on Oct. 10, 2011, now abandoned.

(60) Provisional application No. 61/392,683, filed on Oct. 13, 2010.

(51) Int. Cl.
| | |
|---|---|
| *A61K 39/395* | (2006.01) |
| *C07K 16/24* | (2006.01) |
| *C07H 21/00* | (2006.01) |
| *C12N 15/09* | (2006.01) |
| *A61K 39/00* | (2006.01) |

(52) U.S. Cl.
CPC .......... *C07K 16/248* (2013.01); *C07H 21/00* (2013.01); *C12N 15/09* (2013.01); *A61K 2039/505* (2013.01); *A61K 2039/54* (2013.01); *C07K 2317/14* (2013.01); *C07K 2317/21* (2013.01); *C07K 2317/33* (2013.01); *C07K 2317/526* (2013.01); *C07K 2317/55* (2013.01); *C07K 2317/56* (2013.01); *C07K 2317/565* (2013.01); *C07K 2317/72* (2013.01); *C07K 2317/76* (2013.01); *C07K 2317/92* (2013.01); *C07K 2317/94* (2013.01)

(58) Field of Classification Search
CPC ................................................ A61K 2039/505
See application file for complete search history.

(56) References Cited

U.S. PATENT DOCUMENTS

| | | | |
|---|---|---|---|
| 5,120,535 A | 6/1992 | Marquardt et al. | |
| 5,202,116 A | 4/1993 | Brown et al. | |
| 5,223,409 A | 6/1993 | Ladner et al. | |
| 5,403,484 A | 4/1995 | Ladner et al. | |
| 5,427,908 A | 6/1995 | Dower et al. | |
| 5,428,012 A | 6/1995 | Shoyab et al. | |
| 5,451,506 A | 9/1995 | Shoyab et al. | |
| 5,571,698 A | 11/1996 | Ladner et al. | |
| 5,580,717 A | 12/1996 | Dower et al. | |
| 5,585,793 A | 12/1996 | Antoshenkov et al. | |
| 5,618,715 A | 4/1997 | Shoyab et al. | |
| 5,681,930 A | 10/1997 | Radka et al. | |
| 5,874,536 A | 2/1999 | Linsley et al. | |
| 5,907,033 A | 5/1999 | Radka et al. | |
| 5,958,442 A | 9/1999 | Wallace et al. | |
| 5,969,108 A | 10/1999 | McCafferty et al. | |
| 6,172,197 B1 | 1/2001 | McCafferty et al. | |
| 6,521,404 B1 | 2/2003 | Griffiths et al. | |
| 6,544,731 B1 | 4/2003 | Griffiths et al. | |
| 6,555,313 B1 | 4/2003 | Griffiths et al. | |
| 6,582,915 B1 | 6/2003 | Griffiths et al. | |
| 6,593,081 B1 | 7/2003 | Griffiths et al. | |
| 8,580,714 B2 | 11/2013 | Almagro et al. | |
| 2002/0018750 A1 | 2/2002 | Hansen et al. | |
| 2002/0086978 A1 | 7/2002 | Verhoeyen | |
| 2003/0044772 A1 | 3/2003 | Watkins et al. | |
| 2003/0079253 A1 | 4/2003 | Hiatt et al. | |
| 2004/0208887 A1 | 10/2004 | Drakenberg et al. | |
| 2005/0208558 A1 | 9/2005 | Venter et al. | |
| 2007/0124833 A1 | 5/2007 | Abad et al. | |
| 2007/0218064 A1 | 9/2007 | Benson et al. | |
| 2007/0286861 A1 | 12/2007 | Ellis et al. | |
| 2008/0090999 A1 | 4/2008 | Goldman et al. | |
| 2008/0292620 A1 | 11/2008 | Damiano et al. | |
| 2009/0155164 A1 | 6/2009 | Brasel et al. | |
| 2009/0232795 A1 | 9/2009 | Condra et al. | |
| 2010/0021477 A1 | 1/2010 | Tsui et al. | |

FOREIGN PATENT DOCUMENTS

| | | |
|---|---|---|
| EP | 0 451 612 B1 | 3/1991 |
| WO | WO 90/07861 A1 | 7/1990 |
| WO | WO 99/48523 A2 | 9/1999 |
| WO | WO 2005/095457 A2 | 10/2005 |

(Continued)

OTHER PUBLICATIONS

Al-Lazikani, et al., "Standard Conformations for the Canonical Structures of Immunoglobulins," Journal of Molecular Biology, 273: 927-948 (1997).

Auguste, et al., "Signaling of Type II Oncostatin M Receptor," The Journal of Biological Chemistry, 272(25): 15760-15764 (1997).

Barent, et al., "Membrane glycoprotein gp130 of *Dictyostelium discoideum* is lipid-linked and its fate altered in the presence of tunicamycin," Papers in Microbiology, Sep. 2001.

Bird, et al., "Single-Chain Antigen-Binding Proteins," Science, 242: 423-426 (1988).

Casset, et al., "A peptide mimetic of an anti-CD4 monoclonal antibody by rational design," Biochemical and Biophysical Research Communications, 307: 198-205 (2003).

(Continued)

*Primary Examiner* — Prema Mertz
(74) *Attorney, Agent, or Firm* — Eric Dichter

(57) ABSTRACT

Antibodies and compositions capable of neutralizing oncostatin M biological functions are useful in treating diseases and disorders associated with oncostatin M, such as osteoarthritis and idiopathic pulmonary fibrosis.

4 Claims, 9 Drawing Sheets

Specification includes a Sequence Listing.

(56) References Cited

FOREIGN PATENT DOCUMENTS

| WO | WO 2006/084092 A2 | 8/2006 |
|----|-------------------|--------|
| WO | WO 2009/085462 A1 | 7/2009 |
| WO | WO 2009/086320 A1 | 7/2009 |
| WO | WO 2012/069433 A2 | 5/2012 |

OTHER PUBLICATIONS

Chothia, et al., "Canonical Structures for the Hypervariable Regions of Immunoglobulins," Journal of Molecular Biology, 196: 901-917 (1987).

Co, et al., "Chimeric and Humanized Antibodies with Specificity for the CD33 Antigen," The Journal of Immunology, 148: 1149-1154 (1992).

P.M. Colman, "Effects of amino acid sequence changes on antibody-antigen interactions," Research in Immunology, 145: 33-36 (1994).

Gearing, et al., "The IL-6 Signal Transducer, gp130: An Oncostatin M Receptor and Affinity Converter for the LIF Receptor," Science, 255: 1434-1437 (1992).

Heinrich, et al., "Principles of interleukin (IL)-6-type cytokine signaling and its regulation," Biochemical Journal, 374: 1-20 (2003).

Hoogenboom, et al., "By-passing Immunisation Human Antibodies from Synthetic Repertoires of Germline $V_H$ Gene Segments Rearranged in Vitro," Journal of Molecular Biology, 227: 381-388 (1992).

Huang, et al., "Role of Receptor for Advanced Glycation End-Product (RAGE) and the JAK/STAT-Signaling Pathway in AGE-Induced Collagen Production in NRK-49F Cells," Journal of Cellular Biochemistry, 81: 102-113 (2001).

Huston, et al., "Protein engineering of antibody binding sites: Recovery of specific activity in an anti-digoxin single-chain Fv analogue produced in *Escherichia coli*," Proceedings of the National Academy of Science USA, 85: 5879-5883 (1988).

Kawasaki, et al., "Evolutionary dynamics of the human immunoglobulin κ locus and the germline repertoire of the Vκ genes," European Journal of Immunology, 31: 1017-1028 (2001).

Knappik, et al., "Fully Synthetic Human Combinatorial Antibody Libraries (HuCAL) Based on Modular Consensus Frameworks and CDRs Randomized with Trinucleotides," The Journal of Molecular Biology, 296: 57-86 (2000).

Köhler, et al., "Continuous cultures of fused cells secreting antibody of predefined specificity," Nature, 256: 495-497 (1975).

LeFranc, et al., "IMGT, the international ImMunoGeneTics information system®," Nucleic Acids Research, 33: D593-D597 (2005).

Lim, et al., "Stat3 contributes to keloid pathogenesis via promoting collagen production, cell proliferation and migration," Oncogene, 25: 5416-5425 (2006).

Marks, et al., "By-passing Immunization. Human Antibodies from V-gene Libraries Displayed on Phage," Journal of Molecular Biology, 222: 581-597 (1991).

McCallum, et al., "Antibody-antigen Interactions: Contact Analysis and Binding Site Topography," Journal of Molecular Biology, 262: 732-745 (1996).

Mosley, et al., "Dual Oncostatin M (OSM) Receptors," The Journal of Biological Chemistry, 271: 32635-32643 (1996).

Rudikoff, et al., "Single amino acid substitution altering antigen-binding specificity," Proceedings of the National Academy of Science USA, 79: 1979-1983 (1982).

Queen, et al., "A humanized antibody that binds to the interleukin 2 receptor," Proceedings of the National Academy of Science USA, 86: 10029-10033 (1989).

William E. Paul, M.D., Fv structure and diversity in three dimension, Fundamental Immunology, $3^{rd}$ Ed., Raven Press, New York, Chapter 8, p. 292-295 (1993).

Schäble, et al., "The Variable Genes of the Human Immunoglobulin χ Locus," Biological Chemistry Hoppe-Seyler, 374: 1001-1022 (1993).

Sheets, et al., "Efficient construction of a large nonimmune phage antibody library: The production of high-affinity human single-chain antibodies to protein antigens," Proceedings of the National Academy of Science USA, 95: 6157-6162 (1998).

Shi, et al., "De Novo Selection of High-Affinity Antibodies from Synthetic Fab Libraries Displayed on Phage as pIX Fusion Proteins," The Journal of Molecular Biology, 397: 385-396 (2010).

Sundberg, et al., "Structural Basis of Antibody-Antigen Interactions," Methods in Molecular Biology, 524: 23-36 (2009).

Tanaka, et al., "Oncostatin M, a multifunctional cytokine," Review of Physiological and Biochemical Pharmacology, 149: 39-52 (2003).

Vaughan, et al., Human Antibodies with Sub-nanomolar Affinities Isolated from a Large Non-immunized Phage Display Library, Nature Biotechnology, 14: 309-314 (1996).

Ward, et al., "Binding activities of a repertoire of single immunoglobulin variable domains secreted from *Escherichia coli*," Nature, 341: 544-546 (1989).

Boder, et al., "Directed evolution of antibody fragments with monovalent femtomolar antigen-binding affinity," Proceedings of the National Academy of Science, 97(20): 10701-10705 (2000).

Herren Wu, "Simultaneous Humanization and Affinity Optimization of Monoclonal Antibodies," Methods in Molecular Biology, 207: 197-212.

Retra, et al., "Surface Plasmon Resonance biosensor analysis as a useful tool in FBDD," Drug Discovery Today: Technologies, 7(3): e181-e187 (2010).

Steven Howard, "Fragment-Based Drug Discovery," Royal Society of Chemistry, Drug Discovery Series No. 47, © 2015.

Biacore™ Assay Handbook, GE Healthcare Bio-Sciences AB, 29-0194-00 AA May 2012, pp. 1-6.

Biacore 3000, GE Healthcare Life Sciences, 29-0048-73 AA Sep. 2011, pp. 1-2.

Biacore T100, GE Healthcare, 28-9214-30 AB (Dec. 2008), pp. 1-8.

Oliver, et al., "Identification of a pg130 Cytokine Receptor Critical Site Involved in Oncostatin M Response," The Journal of Biological Chemistry, 275(8): 5648-5656 (2000).

*Fig. 1*

Amino acid sequences and numbering of human germline antibody frameworks used in the library

```
            1          10         20         30         40         50         60         70         80         90        100                  110
            |----------|----------|----------|----------|----------|----------|----------|----------|----------|-----abc--|---abcdef-----------|
IGHV1-69    QVQLVQSGAEVKKPGSSVKVSCKASGGTFSSYAISWVRQAPGQGLEWMGGIIPIFGTANYAQKFQGRVTITADESTSTAYMELSSLRSEDTAVYYCAR-----------------WGQGTLVTVSS 1          10         20         30         40         50         60         70         80         90        100                  110
            |----------|----------|----------|----------|----------|----------|----------|----------|----------|-----abc--|---abcdef-----------|
IGHV3-23    EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAK-----------------WGQGTLVTVSS 1          10         20         30         40         50         60         70         80         90        100                  110
            |----------|----------|----------|----------|----------|--a-------|----------|----------|----------|---abc----|---abcdef-----------|
IGHV5-51    EVQLVQSGAEVKKPGESLKISCKGSGYSFTSYWIGWVRQMPGKGLEWMGIIYPGDSDTRYSPSFQGQVTISADKSISTAYLQWSSLKASDTAMYYCAR-----------------WGQGTLVTVSS 1          10         20         30         40         50         60         70         80         90        100
            |----------|----------|----------|----------|----------|----------|----------|----------|----------|----------|
IGKV3-20 A27 EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPLTFGQGTKVEIK 1          10         20         30         40         50         60         70         80         90        100
            |----------|----------|----------|----------|---abcdef-|----------|----------|----------|----------|----------|
IGKV4-1 B3  DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQYYSTPLTFGQGTKVEIK 1          10         20         30         40         50         60         70         80         90        100
            |----------|----------|----------|----------|----------|----------|----------|----------|----------|----------|
IGKV3-11 L6 EIVLTQSPATLSLSPGERATLSCRASQSVSSYLAWYQQKPGQAPRLLIYDASNRATGIPARFSGSGSGTDFTLTISSLEPEDFAVYYCQQRSNWPLTFGQGTKVEIK 1          10         20         30         40         50         60         70         80         90        100
            |----------|----------|----------|----------|----------|----------|----------|----------|----------|----------|
IGKV1-39 O12 DIQMTQSPSSLSASVGDRVTITCRASQSISSYLNWYQQKPGKAPKLLIYAASSLQSGVPSRFSGSGSGTDFTLTISSLQPEDFATYYCQQYSTPLTFGQGTKVEIK
```

METHOD OF TREATING IDIOPATHIC PULMONARY FIBROSIS BY ADMINISTERING HUMAN ONCOSTATIN M ANTIBODIES

CROSS REFERENCE TO RELATED APPLICATIONS

This application is a divisional of U.S. application Ser. No. 14/870,774, filed 30 Sep. 2015, currently allowed, which is a divisional of U.S. application Ser. No. 14/104,520, filed 12 Dec. 2013, now U.S. Pat. No. 9,163,083, granted 20 Oct. 2015, which is a continuation of U.S. patent application Ser. No. 13/269,976, filed 10 Oct. 2011, now abandoned, which claims the benefit of U.S. Provisional Application Ser. No. 61/392,683, filed 13 Oct. 2010. The entire contents of each of the aforementioned applications are incorporated herein by reference in their entireties.

FIELD OF THE INVENTION

The present invention relates to a human antibody capable of neutralizing the biological activity produced by oncostatin M binding to membrane receptors on human cells, and uses.

BACKGROUND OF THE INVENTION

Oncostatin M (OSM) is a 28 kDa multifunctional member of the IL-6 family of cytokines secreted by monocytes, macrophages, neutrophils and activated T-lymphocytes (Tanaka & Miyajima, *Rev Physiol Biochem Pharmacol* 149: 39-53, 2003). Proteolytic cleavage near the carboxy-terminus of the secreted OSM yields the fully active form of OSM, 209 amino acids length having two N-linked glycosylation sites. OSM belongs to the IL-6 family of cytokines that includes (IL-6, IL-11, leukemia inhibitory factor (LIF), cardiotrophin-1, ciliary neutotrophic factor (CNTF) and cardiotrophin-like cytokine (CLC)) which share a common receptor subunit, gp130 protein. In humans, OSM signals through receptor heterodimers consisting of gp130 and the LIFRα subunit or gp130 and the OSMRβ subunit. In contrast to the other cytokines of the IL-6 family, OSM binds gp130 directly and in the absence of any additional membrane-bound co-receptor (Gearing et al., *Science* 255: 1434-1437, 1992). Following OSM binding to gp130, OSMRβ or LIFRα are recruited to form a high-affinity signaling complex (Mosley et al., *J Biol Chem* 271: 32635-32643, 1996). Activation of either receptor results in signaling via the JAK/STAT pathway (Auguste et al., *J Biol Chem* 272: 15760-15764, 1997).

OSM is produced primarily by cells of immune system origin and, because of the widespread distribution of its signaling receptors, it has been associated with a variety of biological activities, including cell growth regulation, neural development and regulation of extracellular matrix composition.

As its name implies, oncostatin M is associated with oncogenic processes. However, OSM is also involved in early events in inflammatory and hypertrophic pathways leading to deleterious conditions, such as pulmonary fibrosis. Thus, there is a need to provide human antibodies specific for human OSM capable of blocking receptor signaling (gp130 signaling) events which signal blocking antibodies can exert a clinically useful cytotoxic, cytostatic, or immunomodulatory effects on gp130 expressing cells.

SUMMARY OF THE INVENTION

The present invention provides OSM binding, monoclonal antibodies capable of blocking activities associated with one or more bioactivities associated with OSM and OSM binding receptor interaction on cells, tissues, or organs in a host subject. Amino acid sequences of exemplary OSM binding monoclonal antibodies are provided which can be encoded by nucleic acids for expression in a host cell. One or more of the OSM monoclonal antibodies of the invention define an epitope on the surface of OSM which, when engaged by an antibody of the invention, is prevented from interaction with the receptor components of the signaling complex, gp130 and LIFRα or gp130 and OSMRβ, thereby preventing ligand ligation driven signaling and downstream biological activity.

One aspect of the invention is an isolated antibody reactive with human OSM protein having the antigen binding ability of a monoclonal antibody comprising an antigen binding domain comprising amino acid sequences as set forth in SEQ ID NOs: 13-18 alone or at specified positions of FR1-CDR1-FR2-CDR2-FR3 as set forth in SEQ ID NOs: 1-3, a CDR3 as represented by SEQ ID NO: 27-29 and 47; or an antigen binding domain comprising amino acid sequences as set forth in SEQ ID NOs: 23-26 alone or at specified positions as set forth in SEQ ID NOs: 5-8 and variants thereof, and a CDR3 as represented by SEQ ID NO: 19-22. In a specific embodiment, the human OSM binding antibody comprises a variable domain selected from SEQ ID NO: 49-55.

In another embodiment of the invention, the monoclonal antibody binding domains used as full length IgG structures, have constant domains derived from human IgG constant domains or specific variants thereof and are used as therapeutic molecules in a pharmaceutical preparation to prevent binding of OSM to cells displaying OSM receptor components. In another embodiment, the binding domains are configured as antibody fragments for use as a therapeutic molecule capable of prevent binding of OSM to cells displaying OSM receptor components. In one aspect of the invention, there is provided a pharmaceutically acceptable formulation, delivery system, or kit or a method of treating oncostatin M-related conditions comprising one or more of the OSM binding domains of the invention such as but not limited to 13-28 and 30-46 and variants as provided by SEQ ID NO: 29 and 47.

BRIEF DESCRIPTION OF THE SEVERAL VIEWS OF THE DRAWING

FIG. 1 shows the germline gene sequences used to build the Fab libraries displayed on pIX coat protein, wherein each of the HV domains consist of a variegated FR1-CDR1-FR2-CDR2-FR3 according to SEQ ID NO: 1-3 (1=IGHV1-69, 2=IGHV3-23, and 3=IGHV5-51) followed by a variable length, varigated H-CDR3 region, and a J-region (FR4, SEQ ID NO: 4); and each of the LV domains consist of a variegated FR1-CDR1-FR2-CDR2-FR3 according to SEQ ID NO: 5-8 (5=IGKV1-39 (O12), 6=IGKV3-11 (L6), 7=IGKV3-20 (A27), and 8=IGKV4-1 (B3)) followed by a CDR3 according to SEQ ID NO: 9 which is followed by a J-region (FR4, SEQ ID NO: 10).

DETAILED DESCRIPTION OF THE INVENTION

Figure 2A:
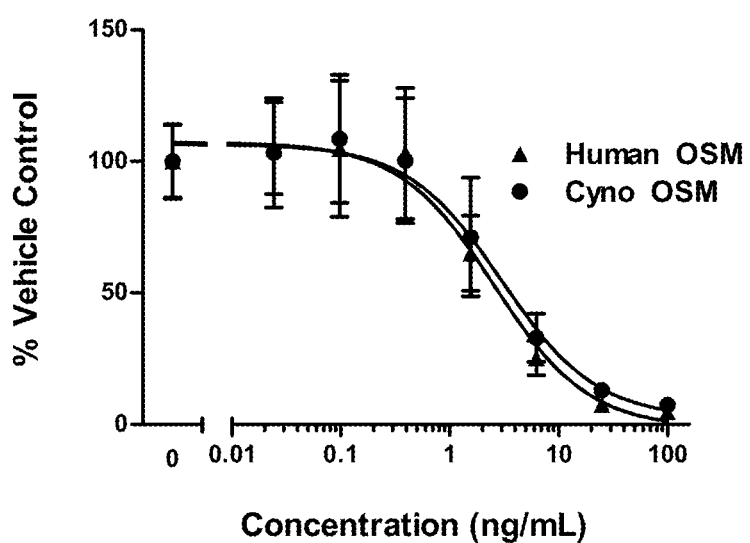
FIG. 2A is a graph of the dose-response of the CHO cell-derived recombinant human and cynomolgous monkey oncostatin M in suppressing proliferation of A375-S2 cells as measured by BrdU incorporation and normalized to the control in the presence of vehicle only.

All publications, including but not limited to patents and patent applications, cited in this specification are herein incorporated by reference as though fully set forth.

Abbreviations

BSA=bovine serum albumin; CDR=complementarity determining region; Cyno=Cynomolgus monkey (*Macaca fascicularis*); DN=diabetic nephropathy; ECD=extracellular domain; FR=framework; H=heavy chain; IPF=interstitial pulmonary arthritis; L=light chain; Ig=immunoglobulin; Mab=monoclonal antibody; OSM=oncostatin M; OA=osteoarthritis; PBS=phosphate buffered saline; RA=rheumatoid arthritis; VL=Variable light chain; VH=Variable heavy chain,

Definitions

As used herein, an "antibody" includes whole antibodies and any antigen binding fragment or a single chain thereof. Thus, the antibody includes any protein or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, which can be incorporated into an antibody of the present invention. The term "antibody" is further intended to encompass antibodies, digestion fragments, specified portions and variants thereof, including antibody mimetics or comprising portions of antibodies that mimic the structure and/or function of an antibody or a specified fragment or portion thereof, including single chain and single domain antibodies and fragments thereof. Functional fragments include antigen-binding fragments to a preselected target. Examples of binding fragments encompassed within the term "antigen binding portion" of an antibody include (i) a Fab fragment, a monovalent fragment consisting of the VL, VH, CL and CH, domains; (ii) a F(ab')2 fragment, a bivalent fragment comprising two Fab fragments linked by a disulfide bridge at the hinge region; (iii) a Fd fragment consisting of the VH and CH, domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (I 988) Science 242:423-426, and Huston et al. (1988) Proc. Natl. Acad Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Conversely, libraries of scFv constructs can be used to screen for antigen binding capability and then, using conventional techniques, spliced to other DNA encoding human germline gene sequences. One example of such a library is the "HuCAL: Human Combinatorial Antibody Library" (Knappik, A. et al. J Mol Biol (2000) 296(1):57-86).

The term "CDR" refers to the complementarity determining region or hypervariable region amino acid residues of an antibody that participate in or are responsible for antigen-binding. The hypervariable regions or CDRs of the human IgG subtype of antibody comprise amino acid residues from residues 24-34 (L-CDR1), 50-56 (L-CDR2) and 89-97 (L-CDR3) in the light chain variable domain and 31-35 (H-CDR1), 50-65 (H-CDR2) and 95-102 (H-CDR3) in the heavy chain variable domain as described by Kabat et al. (1991 Sequences of Proteins of Immunological Interest, 5th Ed. Public Health Service, National Institutes of Health, Bethesda, Md.) and/or those residues from a hypervariable loop (i.e., residues 26-32 (L1), 50-52 (L2) and 91-96 (L3) in the light chain variable domain and 26-32 (H1), 53-55 (H2) or the current H2 Chothia definition of 52-57, and 96-101 (H3) in the heavy chain variable domain as described by (Chothia and Lesk, J. Mol. Biol. 196: 901-917 (1987)). Chothia and Lesk refer to structurally conserved HVs as "canonical structures." Framework or FR1-4 residues are those variable domain residues other than and bracketing the hypervariable regions. The numbering system of Chothia and Lesk takes into account differences in the number of residues in a loop by showing the expansion at specified residues denoted by the small letter notations, e.g., 30a, 30b, 30c, etc. More recently, a universal numbering system has been developed and widely adopted, international ImMunoGeneTics Information System® (IMGT) (LaFranc, et al. 2005. Nucl Acids Res. 33:D593-D597).

Herein, the CDRs are referred to in terms of both the amino acid sequence and the location within the light or heavy chain by sequential numbering. As the "location" of the CDRs within the structure of the immunoglobulin variable domain is conserved between species and present in structures called loops, by using numbering systems that align variable domain sequences according to structural features, CDR and framework residues and are readily identified. This information is used in grafting and replacement of CDR residues from immunoglobulins of one species into an acceptor framework from, typically, a human antibody.

The term "maturation" is applied to directed changes in an antibody variable region for the purpose of altering the properties of the polypeptide. As is known in the art and described herein, a large number of positions in the V-region sequences that can impact recognition of antigen. In nature, antibodies achieve high affinity and specificity by the progressive process of somatic mutation. This process can be imitated in vitro to permit parallel selection and targeted variation while maintaining the sequence integrity of each antibody chain such that they reflect the species, in the present case, a human, antibody, while enhancing affinity or a biophysical parameter such as solubility or resistance to oxidation. The process of making directed changes or "maturation" is typically performed at the level of the coding sequence and can be achieved by creating sublibraries for selection of the enhanced property.

As used herein "OSM" refers to an oncostatin M polypeptide or polynucleotide comprising a coding sequence encoding the OSM polypeptide. Human OSM is the product of the human osm gene (Gene 5008).

The term "epitope" means a protein determinant capable of specific binding to an antibody. Epitopes usually consist of chemically active surface groupings of molecules, such as amino acids or sugar side chains and usually have specific three-dimensional structural characteristics, as well as specific charge characteristics. Conformational and nonconformational epitopes are distinguished in that the binding to the former but not the latter is lost in the presence of denaturing solvents.

As used herein, $K_D$ refers to the dissociation constant, specifically, the antibody $K_D$ for a predetermined antigen, and is a measure of affinity of the antibody for a specific target. High affinity antibodies have a $K_D$ of $10^{-8}$ M or less, more preferably $10^{-9}$ M or less and even more preferably $10^{-10}$ M or less, for a predetermined antigen. The reciprocal of $K_D$ is $K_A$, the association constant. The term "$k_{dis}$" or "$k_2$," or "$k_d$" as used herein, is intended to refer to the dissociation rate of a particular antibody-antigen interaction. The "$K_D$" is the ratio of the rate of dissociation ($k_2$), also called the "off-rate ($k_{off}$)" to the rate of association rate ($k_1$) or "on-rate ($k_{on}$)." Thus, $K_D$ equals $k_2/k_1$ or $k_{off}$ and is expressed as a molar concentration (M). It follows that the smaller the $K_D$, the stronger the binding. Thus, a $K_D$ of $10^{-6}$ M (or 1 microM) indicates weak binding compared to $10^{-9}$ M (or 1 nM).

The terms "monoclonal antibody" or "monoclonal antibody composition" as used herein refer to a preparation of antibody molecules of single molecular composition. A monoclonal antibody composition displays a single binding specificity and affinity for a particular epitope. The term also includes "recombinant antibody" and "recombinant monoclonal antibody" as all antibodies are prepared, expressed, created or isolated by recombinant means, such as (a) antibodies isolated from an animal or a hybridoma prepared by the fusion of antibody secreting animal cells and an fusion partner, (b) antibodies isolated from a host cell transformed to express the antibody, e.g., from a transfectoma, (c) antibodies isolated from a recombinant, combinatorial human or other species antibody library, and (d) antibodies prepared, expressed, created or isolated by any other means that involve splicing of immunoglobulin gene sequences to other DNA sequences. An "isolated antibody," as used herein, is intended to refer to an antibody which is substantially free of other antibodies having different antigenic specificities. An isolated antibody that specifically binds to an epitope, isoform or variant of human OSM may, however, have cross-reactivity to other related antigens, e.g., from other species (e.g., OSM species homologs). Moreover, an isolated antibody may be substantially free of other cellular material and/or chemicals. In one embodiment of the invention, a combination of "isolated" monoclonal antibodies having different specificities are combined in a well defined composition.

As used herein, "specific binding," "immunospecific binding" and "binds immunospecifically" refers to antibody binding to a predetermined antigen. Typically, the antibody binds with a dissociation constant ($K_D$) of $10^{-7}$ M or less, and binds to the predetermined antigen with a $K_D$ that is at least twofold less than its $K_D$ for binding to a non-specific antigen (e.g., BSA, casein, or any other specified polypeptide) other than the predetermined antigen. The phrases "an antibody recognizing an antigen" and "an antibody specific for an antigen" are used interchangeably herein with the term "an antibody which binds specifically to an antigen." As used herein "highly specific" binding means that the relative $K_D$ of the antibody for the specific target epitope is at least 10-fold less than the $K_D$ for binding that antibody to other ligands.

As used herein, "type" refers to the antibody class (e.g., IgA, IgE, IgM or IgG) that is encoded by heavy chain constant region genes. Some antibody classes further encompass subclasses or "isotypes" which are also encoded by the heavy chain constant regions (e.g., IgG1, IgG2, IgG3 and IgG4). Antibodies may be further decorated by oligosaccharides linked to the protein at specific residues within the constant region domains which further enhance biological functions of the antibody. For example, in human antibody isotypes IgG1, IgG3 and to a lesser extent, IgG2, display effector functions as do murine IgG2a antibodies.

By "effector" functions or "effector positive" is meant that the antibody comprises domains distinct from the antigen specific binding domains capable of interacting with receptors or other blood components such as complement, leading to, for example, the recruitment of macrophages and events leading to destruction of cells bound by the antigen binding domains of the antibody. Antibodies have several effector functions mediated by binding of effector molecules. For example, binding of the C1 component of complement to antibodies activates the complement system. Activation of complement is important in the opsonisation and lysis of cell pathogens. The activation of complement stimulates the inflammatory response and may also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

The term "polypeptide" means a molecule that comprises amino acid residues linked by a peptide bond to form a polypeptide. Small polypeptides of less than 50 amino acids may be referred to as "peptides." Polypeptides may also be referred as "proteins."

Overview

The present invention provides isolated Mabs capable of binding and neutralizing the biological activity of OSM proteins and cleavage products. In particular, the OSM binding mAbs of the invention are able to block OSM binding to gp130 or prevent the recruitment of LIFRα or OSMRb by OSM bound gp130. In either case, the OSM mAb of the invention is capable of blocking OSM driven gp130 receptor signaling.

Phosphorylation of STAT3 has been reported to lead to over-production of collagen by fibroblasts in a variety of pathological contexts (Lim et al. Oncogene 23(39): 5416-25, 2006; Huang et al. J Cell Biochem 81(1): 102-13, 2001). These properties demonstrate the potential therapeutic value of these antibodies for RA, OA and for fibrotic indications such as idiopathic pulmonary fibrosis (IPF) and diabetic nephropathy (DN).

The human OSM gene product, OSM (NCBI Accession No. NP_065391) is a pre-pro-polypeptide 252 amino acids in length (SEQ ID NO: 11), having a signal peptide 25 amino acids in length and a proteolytic cleavage site between residues 234 and 235. It is a secreted protein having five cysteine residues forming two internal disulfides between residues 31 to 152 and 74 to 192 (Kallestad J C, et al. J Biol Chem. 1991 May 15; 266 (14):8940-5). There are two potential N-linked glycosylation sites at residues 100 and 217, and when produced in eukaryotic cells, the protein is glycosylated. The human OSM has a free sulfhydryl at residue 105.

The sequence of cyno OSM protein was not available in the public domain although an automated computationally generated record for an 1867 bp mRNA (NCBI No. XM_001110148) derived from an annotated genomic sequence (NW_001095169) existed. To obtain the cyno OSM sequence, RNA was isolated from cyno PBMC and the gene was then amplified from this cDNA by RT-PCR and sequenced. The predicted translation of the cloned sequence (SEQ ID NO: 12) was found to be 99.6% identical to the predicted Macaca mullata (Rhesus) sequence, 92% identical to the human OSM protein sequence, and 41% identical to the mouse OSM protein sequence as disclosed in applicants copending application (U.S. Ser. No. 12/648,430).

Therefore, the present invention is directed toward the identification of human derived OSM-binding Mabs capable of inhibiting downstream biologic activity resulting from OSM bound gp130 signaling and wherein the Mabs exhibit the ability to;
restore proliferation of cells in the presence of OSM, inhibit OSM-driven chondrocyte degradation of intra-articular (joint) matrix in tissue explants, efficiently neutralize OSM-dependent STAT3 phosphorylation in human lung fibroblasts and prevent OSM induced cytokine release.

1. Composition of an Antibody of the Invention

An OSM-neutralizing antibody of the invention is an antibody that inhibits, blocks, or interferes with at least one OSM activity or OSM receptor binding, in vitro, in situ and/or in vivo and does not promote, stimulate, induce, or agonize OSM activity or ligand binding nor does antibody binding mimic the downstream effects of OSM-driven ligation of OSM receptors, in particular gp130 interaction with OSM, such as signal transduction in a host cell. A suitable OSM-neutralizing antibody, specified portion, or variant can also, optionally, affect at least one OSM activity or function, such as but not limited to; RNA, DNA or protein synthesis; protein release; cell activation, proliferation or differentiation; antibody secretion; OSM receptor signaling; OSM cleavage; OSM binding, OSM or gp130 induction, synthesis or secretion.

The present invention is based upon the discovery of anti-human OSM monoclonal antibodies capable of inhibiting gp130 signaling after OSM binding or LIFR recruitment by OSM. Antibody binding domains in the form of a Fab library displayed on filamentous phage particles linked to the pIX coat protein (see WO29085462A1 and further described hereinbelow) were selected for the ability to bind OSM. A competition assay using gp130 was used to distinguish those Fabs that, when bound to OSM, prevented OSM from binding gp130. Alternatively, Fabs were able to prevent LIFR recruitment to gp130 binding when bound to OSM. A cell-based (A375, human melanoma cell) assay was used to identify several candidate antibodies capable of inhibiting gp130-mediated pSTAT3 activation of OSM expressing host cells.

The OSM-binding antibodies described herein recognize at least two distinct regions on the active form of human OSM protein, indicating the additional discovery of multiple sites on OSM suitable for the targeting of antibodies or other compounds with similar function blocking capabilities. Thus, expression and purification of the antibody binding domains provided herein as amino acid sequences further provides a tool which can provide the means for selection of novel molecules exhibiting OSM-neutralizing activity.

In one embodiment, the anti-human OSM antibody, has a binding region comprising a light chain variable (VL) or heavy chain variable (VH) region comprising the amino acid sequence as shown in SEQ ID NO: 49-55, and which antibody or binding portion thereof immunospecifically binds OSM. In another embodiment of the invention, comprising a heavy chain comprising SEQ ID NO: 54 or 55 an antigen binding portion thereof, binds to OSM protein and, additionally, has the specified functional properties of antibodies of the invention, such as:

1. binds human OSM with a $K_D$ of less than 100 pM
2. binds cyno OSM with a $K_D$ of less than 500 pM
3. Is capable of restoring proliferation of A375-S2 cells in the presence of 2 ng/ml human OSM by 90% of the level in the absence of OSM,
4. Is capable of restoring proliferation of A375-S2 cells in the presence of 2 ng/ml cyno OSM by 90% of the level in the absence of OSM,
5. inhibits OSM-driven chondrocyte degradation of intra-articular (joint) matrix in tissue explants,
6. efficiently neutralizes OSM-dependent STAT3 phosphorylation in normal human lung fibroblasts (NHLF), or
7. blocks cytokine release after systemic challenge with OSM in mice.

In another aspect of the invention, the structural features of the antibodies exhibiting some or all of the above referenced biological activity as described herein and, in particular, the Mabs designated as M55 and M71 binding domains, are used to create structurally related human anti-OSM antibodies that retain at least one functional property of the antibodies of the invention, such as binding to OSM. More specifically, one or more CDR regions of M55 and M71 (such as specified residues of SEQ ID NO: 1 and 8) can be combined recombinantly with known human framework regions and CDRs such as SEQ ID NO: 13-28, 30-46 to create additional, recombinantly-engineered, human anti-OSM antibodies of the invention.

In one embodiment, the antibodies of the invention have the sequences, including FR1, 2, and/or 3; of IGVH1-69

(SEQ ID NO: 1) or of IGVH5-51 (SEQ ID NO: 3), wherein one or more residues from CDRs selected from the group consisting of SEQ ID NO: 13-22 are present in the CDR position of SEQ ID NO: 1 or 3, while still retaining the ability of the antibody to bind OSM (e.g., conservative substitutions). Accordingly, in another embodiment, the engineered antibody may be composed of one or more CDRs that are, for example, 90%, 95%, 98% or 99.5% identical to the CDRs listed in SEQ ID NOs: 13-22 or the variants of L-CDR3 as given by SEQ ID NO: 29 or 47.

In addition to simply binding OSM, engineered antibodies, such as those described above, may be selected for their retention of other functional properties of antibodies of the invention, such as the ability to inhibit binding of OSM protein or a cleavage product thereof to GP130 positive cells to, which binding would result in suppression of proliferation of the GP130 positive cells in vivo.

Human monoclonal antibodies of the invention can be tested for binding to OSM by, for example, standard ELISA.

2. Generation of OSM-Neutralizing Antibodies

A OSM-neutralizing antibody exhibiting the desired bioactivity spectrum as exemplified herein by M5, M6, M9, M10, M42, M45, M53, M54, M55, M62, M63, M65, M66, M67, M68, M69, M71, and M83 comprising the heavy chain and light chain sequences as specified which comprise the library frameworks SEQ ID NOS: 1, 3, 8, and having CDRs of SEQ ID NOS: 13-28, 30-46 can be generated by a variety of techniques.

In another embodiment, the epitope bound by the antibodies of the invention, comprising as few as five to all of residues 51-227 of SEQ ID NO: 11 or a nucleic acid coding sequence therefore, can be used to immunize a subject in order to produce the antibodies of the invention directly in the host for the purpose of treating, preventing, or ameliorating disease or symptoms of disease associated with the production of OSM.

In one embodiment and as exemplified herein, the human antibody is selected from a phage library, where that phage comprises human immunoglobulin genes and the library expresses human antibody binding domains as, for example, single chain antibodies (scFv), as Fabs, or some other construct exhibiting paired or unpaired antibody variable regions (Vaughan et lo al. Nature Biotechnology 14:309-314 (1996): Sheets et al. PITAS (USA) 95:6157-6162 (1998)); Hoogenboom and Winter, J. Mol. Biol., 227:381 (1991); Marks et al. J. Mol. Biol., 222:581 (1991)). Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571, 698 to Ladner et al.; U.S. Pat. Nos. 5,427,908 and 5, 580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Phage clones are selected by and identified through a multi-step procedure known as biopanning. Biopanning is carried out by incubating phage displaying protein ligand variants (a phage display library) with a target, removing unbound phage by a washing technique, and specifically eluting the bound phage. The eluted phage are optionally amplified before being taken through additional cycles of binding and optional amplification that enriches the pool of specific sequences in favor of those phage clones bearing antibody fragments that display the best binding to the target. After several rounds, individual phage clones are characterized, and the sequences of the peptides displayed by the clones are determined by sequencing the corresponding DNA of the phage virion.

Fab Phage-pIX Library

In a specific embodiment of the phage display technology, a synthetic Fab library displayed on the pIX phage coat protein, described in Shi et al. J Mol Biol 397:385-396, 2010; WO29085462A1 and U.S. Ser. No. 12/546,850 and to be further detailed herein, is used to select binder from a repertoire of human IgG sequences derived from human germline genes. Libraries were constructed on four VL and three VH domains encoded by known IGV and IGJ germline sequences selected based on the frequency which the sequences have been observed to be present in human antibodies isolated from natural sources. The VH, IMGT nomenclature, selected are IGHV1-69 (SEQ ID NO: 1), IGHV3-23 (SEQ ID NO: 2), or IGHV5-51 (SEQ ID NO: 3). The diversity in the VH design produces heavy chains with variable length sequence in the CDR3 region with limited diversity positions in the H-CDR1 and H-CDR2 which remain at a constant length. Framework four (H-FR4) is held constant among all members of the library (SEQ ID NO: 4).

VH169, IGHV1-69*01 Length=98, CDR1=31-35, CDR2=50-66

(SEQ ID NO: 1)
QVQLVQSGAE VKKPGSSVKV SCKASGGTFS SYX$_1$ISWVRQA

PGQGLEWMGX$_2$ IX$_3$X$_4$X$_5$X$_6$GTANY AQKFQGRVTI TADESTSTAY

MELSSLRSED TAVYYCAR

Where, in the 169 library $X_1$ is A or G, $X_2$ is G or W, $X_3$ may be I or S, $X_4$ may be P or A, $X_5$ may be I or Y and $X_6$ may be F or N.

VH323, IGHV3-23*01 Length=98, CDR1=31-35, CDR2=50-66

(SEQ ID NO: 2)
EVQLLESGGG LVQPGGSLRL SCAASGFTFS X$_1$YX$_2$MX$_3$WVRQA

PGKGLEWVSX$_4$ IX$_5$X$_6$X$_7$GX$_8$STYY ADSVKGRFTI SRDNSKNTLY

LQMNSLRAED TAVYYCAK

Where, in the 323 library, $X_1$ may be S, D, N, or T; $X_2$ may be A, G, or W; $X_3$ may be S or H; $X_4$ may by V, A, N or G; $X_5$ may be S, N, K or W; $X_6$ may be Y, S, G, or Q; $X_7$ may be S or D; and $X_8$ may be S or G.

VH551, IGHV5-51*03 Length=98, CDR1=31-35, CDR2=50-66

(SEQ ID NO: 3)
EVQLVQSGAE VKKPGESLKI SCKGSGYSFT X$_1$YWIX$_2$WVRQM

PGKGLEWMGX$_3$ IX$_4$PX$_5$DSX$_6$TRY SPSFQGQVTI SADKSISTAY

LQWSSLKASD TAMYYCAR

Where in the 551 library, $X_1$ may be S, N, or T; $X_2$ may be S or G; $X_3$ may be I or R; $X_4$ may by D or Y; $X_5$ may be G or S; $X_6$ may be D or Y.

A FR4 or JH region having (11 residues), WGQGTLVT-VSS (SEQ ID NO: 4), has been joined to the above sequences to form a complete heavy chain variable region.

The H-CDR1 and H-CDR2 positions that were targeted for diversification were determined by 1) diversity in germline genes; and 2) frequency found in contact with antigen in antibody-antigen complexes of known structure (Almagro J Mol Recognit.17:132-143, 2004). The amino acid diversity at the selected positions was determined by 1) usage in germline; 2) amino acids that are most frequently observed in human rearranged V genes; 3) amino acids predicted to be result from single base somatic mutations; and 4) biochemical and biophysical properties of amino acids that contribute to antigen recognition.

The library incorporates diversity in the CDR3 of the VH (H3) mimicking the repertoire of human antibodies (Shi et al. 2010 supra) as shown below (FORMULA I) where the final length is between 7 and 14 residues. Among the CDR3 of over 5000 human variable regions, amino acids glycine (G) and alanine (A) are frequently used in all positions. In addition, aspartic acid (D) is frequently used in position 95 and tyrosine (Y) is frequently encoded in the positions preceding the canonical region of the J segment. Amino acids phenylalanine (F), aspartic acid (D) and tyrosine (Y) predominate at positions 99-101 used in IgGs at these positions. Since these positions often serve as structural support to H-CDR3 and are less accessible to antigen and/or to surface of IgG, amino acids phenylalanine plus leucine (50/50 ratio) at position 99, aspartic acid at position 100 and tyrosine at position 101 were fixed. Thus, the sequence of Formula I is inserted between SEQ ID NOS: 1, 2, or 3 and SEQ ID NO: 4 to create a complete VH.

$$-(D)-(N)n(N+O)m(F)DY- \quad (I)$$

Where:
(D)=Asp (D) and Gly (G) rich position.
(N)n=Ala (A) and Gly (G) rich position, n=3-7.
(O)m=Ala (A), Gly (G) and Y (Tyr) rich in, m=1-4.
(F)=The Phe (F) dominant position.

Various versions of the library encompass pairings with fixed or diversified light chains derived also from the human germline repertoire. In the present invention, the four light-chain library $VL_{kappa}$ genes (Kawasaki et al. 2001. Eur J Immunol 31: 1017-1028 and after Schaeble & Zachau, 1993 Biol Chem Hoppe Seyler 374: 1001-1022) are A27 (IGKV3-20*01), B3 (IGKV4-1*01), L6 (IGKV3-11*01), and O12 (IGKV1-39*01) where the gene name in parentheses are the presumed corresponding IMGT gene. The Fabs are displayed on pIX via expression of a dicistronic vector wherein the VH-CH1 domain is fused to the coat protein sequence and the VL-CLkappa or VL-CLlambda is expressed as a free polypeptide which self-associates with the VH-CH1. The CDR regions are underlined.

Light Chain Variable Library Based on Vkappa (Vk) Germline Genes

O12; IGKV1-39*01, IGKV1D-39*01 Length=88; CDR1=24-34, CDR2=50-56

(SEQ ID NO: 5)
DIQMTQSPSS LSASVGDRVT ITC<u>RASQSIS X₁X₂X₃</u>NWYQQKP

GKAPKLLIY<u>X₄ ASSLQSGVPS</u> RFSGSGSGTD FTLTISSLQP

EDFATYYC

L6, IGKV3-11*01 Length=88, CDR1=24-34, CDR2=50-56

(SEQ ID NO: 6)
EIVLTQSPAT LSLSPGERAT LS<u>CRASQSV X₁X₂X₃LA</u>WYQQKP

GQAPRLLIY<u>X₄ ASNRATGIPA</u> RFSGSGSGTD FTLTISSLEP

EDFAVYYC

A27, IGKV3-20*01, Length=89, CDR1=24-35, CDR2=51-57

(SEQ ID NO: 7)
EIVLTQSPGT LSLSPGERAT LS<u>CRASQSVX₁ X₂X₃X₄LA</u>WYQQK

PGQAPRLLIY <u>X₅ASSRAT</u>GIP DRFSGSGSGT DFTLTISRLE

PEDFAVYYC

B3, DPK24, VKIVKlobeck; IGKV4-1*01 Length=94, CDR1=24-40, CDR2=56-62

(SEQ ID NO: 8)
DIVMTQSPDS LAVSLGERAT INC<u>KSSQSVL X₁SSNNX₂NX₃LA</u>

WYQQKPGQPP KLLIY<u>X₄ASTR ES</u>GVPDRFSG SGSGTDFTLT

ISSLQAEDVA VYYC

The diversity at the specified positions for each variable region scaffold are summarized in Table 1 below where the amino acids single-letter code is used and is present in the alternative at the specified positions as shown in FIG. 1.

TABLE 1

| CDR | Kabat Position | O12 (SEQ ID NO: 5) | L6 (SEQ ID NO: 6) | A27 (SEQ ID NO: 7) | B3 (SEQ ID NO: 8) |
|---|---|---|---|---|---|
| 1 | 30 | $X_1$ SRNAD | $X_1$SRNAD | $X_1$SRNTD | L |
|  | 30a | — | — | $X_2$SNR | $X_1$YSHFA |
|  | 30e | — | — | — |  |
|  | 30f |  |  |  | $X_2$KTNE |
|  | 31 | $X_2$ SNKDG | $X_2$NSKD | $X_3$SNRADH | N |
|  | 32 | $X_3$ YHNDWF SAV | $X_3$YWDFH SAN | $X_4$YFHQSEK | $X_3$YFHNWDAS |
| 2 | 50 | $X_4$ FYTNKA DG | $X_4$ADKGY FTN | $X_5$ADGS | $X_4$WSRDYA |

The VL CDR3 in all of the libraries has seven residues wherein the first two residues are glutamine (Gln, Q) and the residue corresponding to Kabat residue 95 is proline (Pro, P). For L-CDR3 the sequence corresponds to $QQX_1X_2X_3X_4PX_5T$ (SEQ ID NO: 9), where varigation are as in the table below and at the residue positions are according to Kabat.

TABLE 2

| Residue | Kabat CDR3 Position | O12 | L6 | A27 | B3 |
|---|---|---|---|---|---|
| $X_1$ | 91 | SAYHPD | RYSGF | YSHA | YSHA |
| $X_2$ | 92 | FIYHNDKGRE | RHNSL | YNDSHIFKG | YNDSHIFKG |
| $X_3$ | 93 | STHNDRG | NDKR | SNTDGHR | SNTDGHR |
| $X_4$ | 94 | TYLVFSRGPI | WA | TYLVFAS | TYLVFAS |
| $X_5$ | 96 | LWRFYIN | WYFLIR | WYFLIR | WYFLIR |

As the variable sequence varies in length from gene to gene, diversity in a particular residue location within a hypervariable loop or CDR can be described as follows using the residue numbering as defined in Al-Lazikani B, Lesk A M, Chothia C, 1997 (Standard conformations for the canonical structures of immunoglobulins. J Mol Biol 273: 927-948). In this system, the changes in length of the hypervariable loops are accommodated by the designation of subpositions a, b, c, etc. for a given residue.

A framework 4 (FR4) segment such as JK4, FGQGTK-VEIK (SEQ ID NO: 10) was used to form a complete human light chain variable region.

Fab affinity for diverse protein targets from 0.2 to 20 nM has been demonstrated in initial selections.

Methods for an integrated maturation process for improving binding parameters consisting of reshuffling VL or VH diversity or, alternatively, directed or limited VL modification are accomplished using the vectors and primers designed and used for the libraries as described in the referenced publication, as taught herein, and combined with what it known in the art.

Alternative Sources of OSM-binding Immunoglobulin Domains

OSM binding antibodies with the characteristics of the human Mabs disclosed herein may be made or binding fragments sourced from immunoglobulin domains formed by a number of methods, including the standard somatic cell hybridization technique (hybridoma method) of Kohler and Milstein (1975) Nature 256:495. In the hybridoma method, a mouse or other appropriate host animal, such as a hamster or macaque monkey, is immunized as described herein to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp.59-103 (Academic Press, 1986)).

An OSM-neutralizing antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-OSM antibody can be isolated from such animals and immortalized using suitable methods, such as the methods described herein. Alternatively, the antibody coding sequences may be cloned, introduced into a suitable vector, and used to transfect a host cell for expression and isolation of the antibody by methods taught herein and those known in the art.

The use of transgenic mice carrying human immunoglobulin (Ig) loci in their germline configuration provide for the isolation of high affinity fully human monoclonal antibodies directed against a variety of targets including human self antigens for which the normal human immune system is tolerant (Lonberg, N. et al., U.S. Pat. No. 5,569,825, U.S. Pat. No. 6,300,129 and 1994, Nature 368:856-9; Green, L. et al., 1994, Nature Genet. 7:13-21; Green, L. & Jakobovits, 1998, Exp. Med. 188:483-95; Lonberg, N and Huszar, D., 1995, Int. Rev. Immunol. 13:65-93; Kucherlapati, et al. U.S. Pat. No. 6,713,610; Bruggemann, M. et al., 1991, Eur. J. Immunol. 21:1323-1326; Fishwild, D. et al., 1996, Nat. Biotechnol. 14:845-851; Mendez, M. et al., 1997, Nat. Genet. 15:146-156; Green, L., 1999, J. Immunol. Methods 231:11-23; Yang, X. et al., 1999, Cancer Res. 59:1236-1243; Brüggemann, M. and Taussig, M J., Curr. Opin. Biotechnol. 8:455-458, 1997; Tomizuka et al. WO02043478). The endogenous immunoglobulin loci in such mice can be disrupted or deleted to eliminate the capacity of the animal to produce antibodies encoded by endogenous genes. In addition, companies, such as Abgenix, Inc. (Freemont, Calif.) and Medarex (San Jose, Calif.) can be engaged to provide human antibodies directed against a selected antigen using technology as described above.

Preparation of polypeptides for use as target ligands in panning strategies and as immunogenic antigens can be performed using any suitable technique, such as recombinant protein production. The target ligand or fragment thereof in the form of purified protein, or protein mixtures including whole cells or cell or tissue extracts, or, in the case of an immunization, the antigen can be formed de novo in the animal's body from nucleic acids encoding said antigen or a portion thereof.

The isolated nucleic acids of the present invention can be made using (a) recombinant methods, (b) synthetic techniques, (c) purification techniques, or combinations thereof, as well-known in the art. DNA encoding the monoclonal antibodies is readily isolated and sequenced using methods known in the art (e.g., by using oligonucleotide probes that are capable of binding specifically to genes encoding the heavy and light chains of human antibody regions). Where a hybridoma is produced, such cells can serve as a source of such DNA. Alternatively, using display techniques wherein the coding sequence and the translation product are linked, such as phage or ribosomal display libraries, the selection of the binder and the nucleic acid is simplified. After phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria.

Human Antibodies

The invention further provides human immunoglobulins (or antibodies) which bind human OSM. These antibodies can also be characterized as engineered or adapted. The immunoglobulins have variable region(s) substantially from a human germline immunoglobulin and include directed variations in residues known to participate in antigen recognition, e.g. the CDRs of Kabat or the hypervariable loops as structurally defined. The constant region(s), if present, are also substantially from a human immunoglobulin. The human antibodies exhibit $K_D$ for OSM of at least about $10^{-6}$ M (1 microM), about $10^{-7}$M (100 nM), $10^{-9}$ M (1 nM), or less. To affect a change in affinity, e.g., improve affinity or reduce $K_D$, of the human antibody for OSM, substitutions in either the CDR residues or other residues may be made.

The source for production of human antibody which binds to OSM is preferably the sequences provide herein as the variable regions, frameworks and/or CDRs, noted as SEQ ID NO: 13-55 identified as capable of binding human OSM and cross-reacting with cynomolgous monkey OSM using a repertoire of human derived Fab displayed on filamentous phage particles.

The substitution of any of the CDRs into any human variable domain framework is most likely to result in retention of their correct spatial orientation if the human variable domain framework adopts the same or similar conformation to the parent variable framework from which the CDRs originated. The heavy and light chain variable framework regions to be paired in the final Mab can be derived from the same or different human antibody sequences. The human antibody sequences can be the sequences of naturally occurring human antibodies, be derived from human germline immunoglobulin sequences, or can be consensus sequences of several human antibody and/or germline sequences.

Suitable human antibody sequences are identified by computer comparisons of the amino acid sequences of the mouse variable regions with the sequences of known human antibodies. The comparison is performed separately for heavy and light chains but the principles are similar for each.

With regard to the empirical method, it has been found to be particularly convenient to create a library of variant sequences that can be screened for the desired activity, binding affinity or specificity. One format for creation of such a library of variants is a phage display vector. Alternatively, variants can be generated using alternate and known methods for randomizing or variegating a nucleic acid sequence encoding the targeted residues within the variable domain.

Another method of determining whether further substitutions are required, and the selection of amino acid residues for substitution, can be accomplished using computer modeling. Computer hardware and software for producing three-dimensional images of immunoglobulin molecules are widely available. In general, molecular models are produced starting from solved structures for immunoglobulin chains or domains thereof. The chains to be modeled are compared for amino acid sequence similarity with chains or domains of solved three dimensional structures, and the chains or domains showing the greatest sequence similarity is/are selected as starting points for construction of the molecular model. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

Because of the degeneracy of the code, a variety of nucleic acid sequences will encode each immunoglobulin amino acid sequence. The desired nucleic acid sequences can be produced by de nova solid-phase DNA synthesis or by PCR mutagenesis of an earlier prepared variant of the desired polynucleotide. All nucleic acids encoding the antibodies described in this application are expressly included in the invention.

The variable segments of human antibodies produced as described herein are typically linked to at least a portion of a human immunoglobulin constant region. The antibody will contain both light chain and heavy chain constant regions. The heavy chain constant region usually includes CH1, hinge, CH2, CH3, and, sometimes, CH4 domains.

The human antibodies may comprise any type of constant domains from any class of antibody, including IgM, IgG, IgD, IgA and IgE, and any subclass (isotype), including IgG1, IgG2, IgG3 and IgG4. When it is desired that the humanized antibody exhibit cytotoxic activity, the constant domain is usually a complement-fixing constant domain and the class is typically $IgG_1$. When such cytotoxic activity is not desirable, the constant domain may be of the $IgG_2$ class. The humanized antibody may comprise sequences from more than one class or isotype.

Nucleic acids encoding humanized light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Such control sequences include a signal sequence, a promoter, an enhancer, and a transcription termination sequence (see Queen et al., Proc. Natl. Acad. Sci. USA 86, 10029 (1989); WO 90/07861; Co et al., J. Immunol. 148, 1149 (1992), which are incorporated herein by reference in their entirety for all purposes).

3. Methods of Using an Anti-OSM Antibody

As described in detail below, the present invention demonstrates that isolated monoclonal antibodies having the variable domains of M5, M6, M9, M10, M42, M45, M53, M54, M55, M62, M63, M65, M66, M67, M68, M69, M71, and M83 bind overlapping epitopes on OSM and display in vitro and/or in vivo OSM inhibiting activities. Significantly, the reactivity of the selected MAbs includes the ability to dose-dependently block OSM interaction with gp130, reduce OSM signaling in the presence of gp130, reduce OSM-stimulated proliferation of A375 cells, prevent macrophage-stimulated chondrocyte collagen production, or reduce cytokine release by OSM in vivo.

Given the properties of the monoclonal antibodies as described in the present invention, the antibodies or antigen binding fragments thereof are suitable both as therapeutic and prophylactic agents for treating or preventing OSM-associated conditions in humans and animals.

In general, use will comprise administering a therapeutically or prophylactically effective amount of one or more monoclonal antibodies or antigen binding fragments of the present invention, or an antibody or molecule selected to have similar spectra of binding and biologic activity, to a susceptible subject or one exhibiting a condition in which OSM activity is known to have pathological sequelae, such as immunological disorders or tumor growth and metastasis. Any active form of the antibody can be administered, including Fab and F(ab')2 fragments.

Preferably, the antibodies used are compatible with the recipient species such that the immune response to the MAbs does not result in an unacceptably short circulating half-life or induce an immune response to the MAbs in the subject. The MAbs administered may exhibit some secondary functions, such as binding to Fc receptors of the subject and activation of ADCC mechanisms, in order to deplete the target cell population using cytolytic or cytotoxic mechanisms or they may be engineered to by limited or devoid of these secondary effector functions in order to preserve the target cell population.

Treatment of individuals may comprise the administration of a therapeutically effective amount of the antibodies of the present invention. The antibodies can be provided in a kit as described below. The antibodies can be used or administered as a mixture, for example, in equal amounts, or individually, provided in sequence, or administered all at once. In providing a patient with antibodies, or fragments thereof, capable of binding to OSM, or an antibody capable of protecting against OSM in a recipient patient, the dosage of administered agent will vary depending upon such factors as the patient's age, weight, height, sex, general medical condition, previous medical history, etc.

In a similar approach, another therapeutic use of the monoclonal antibodies of the present invention is the active immunization of a patient using an anti-idiotypic antibody raised against one of the present monoclonal antibodies. Immunization with an anti-idiotype which mimics the structure of the epitope could elicit an active anti-OSM response (Linthicum, D. S. and Farid, N. R., Anti-idiotypes, Receptors, and Molecular Mimicry (1988), pp 1-5 and 285-300).

Likewise, active immunization can be induced by administering one or more antigenic and/or immunogenic epitopes as a component of a vaccine. Vaccination could be performed orally or parenterally in amounts sufficient to enable the recipient to generate protective antibodies against this biologically functional region, prophylactically or therapeutically. The host can be actively immunized with the antigenic/immunogenic peptide in pure form, a fragment of the peptide, or a modified form of the peptide. One or more amino acids, not corresponding to the original protein sequence can be added to the amino or carboxyl terminus of the original peptide, or truncated form of peptide. Such extra amino acids are useful for coupling the peptide to another peptide, to a large carrier protein, or to a support. Amino acids that are useful for these purposes include: tyrosine, lysine, glutamic acid, aspartic acid, cysteine and derivatives thereof. Alternative protein modification techniques may be used, e.g., NH2-acetylation or COOH-terminal amidation, to provide additional means for coupling or fusing the peptide to another protein or peptide molecule or to a support.

The antibodies capable of protecting against unwanted OSM bioactivity are intended to be provided to recipient subjects in an amount sufficient to effect a reduction, resolution, or amelioration in the OSM-related symptom or pathology. An amount is said to be sufficient or a "therapeutically effective amount" to "effect" the reduction of symptoms if the dosage, route of administration, etc. of the agent are sufficient to influence such a response. Responses to antibody administration can be measured by analysis of subject's affected tissues, organs, or cells as by imaging techniques or by ex vivo analysis of tissue samples. An agent is physiologically significant if its presence results in a detectable change in the physiology of a recipient patient.

Therapeutic Applications

The OSM-neutralizing antibodies of the present invention, antigen binding fragments, or specified variants thereof can be used to measure or cause effects in an cell, tissue, organ or animal (including mammals and humans), to diagnose, monitor, modulate, treat, alleviate, help prevent the incidence of, or reduce the symptoms of, a condition mediated, affected or modulated by OSM or cells expressing OSM. Thus, the present invention provides a method for modulating or treating at least one OSM related disease, in a cell, tissue, organ, animal, or patient, as known in the art or as described herein, using at least one OSM antibody of the present invention.

OSM is known to be up-regulated in a variety of disease states that involve inflammation and has been implicated in diverse biological roles including bone formation, cartilage degradation, cholesterol uptake, pain, and inflammation. Particular indications are discussed below.

Indications

The present inventors have demonstrated that OSM mediates cartilage destruction and shown that OSM causes chondrocyte degradation in intra-articular matrix from tissue explants. OSM also promotes cytokine release, such as TNFα, which is able to promote collagen release from cartilage as shown by T. Cawston et al (1998, Arthritis and Rheumatism, 41(10) 1760-1771) and that presently an antibody exemplified as M71 binding domains is capable of blocking systemic cytokine release. An antibody of the present invention; M55, M64, M69, and M71 demonstrated the ability to increase proteoglycan synthesis in a macrophage-chondrocyte co-culture system above the level seen in the absence of an OSM-specific antibody.

The present inventors have further demonstrated that administration of a neutralising anti-OSM antibody of the invention will inhibit OSM driven cytokine and chemokine release in vivo, such as IL-6, IP-10, and KC. IP-10, interferon gamma-induced protein 10 kDa or small-inducible cytokine B10, is a protein that in humans is encoded by the CXCL10 gene (C-X-C motif chemokine 10 (CXCL10). CXCL10 has been attributed to several roles, such as chemoattraction for monocytes/macrophages, T cells, NK cells, and dendritic cells, and promotion of T cell adhesion to endothelial cells. KC, now known as chemokine (C-X-C motif) ligand 1 (CXCL1), is a small cytokine belonging to the CXC chemokine family that was previously called GRO1 oncogene, GROα, Neutrophil-activating protein 3 (NAP-3) and melanoma growth stimulating activity, alpha (MSGA-α). In humans, this protein is encoded by the CXCL1 gene. CXCL1 is expressed by macrophages, neutrophils and epithelial cells, and has neutrophil chemoattractant activity.

According to the present invention there is therefore provided the use of an antibody or antibody fragment selected from the group M5, M6, M9, M10, M42, M45, M53, M54, M55, M62, M63, M65, M66, M67, M68, M69, M71, and M83 in the manufacture of a medicament for the treatment or prophylaxis of an articular proteoglycan degradative disease such as osteoarthritis, an inflammatory arthropathy or inflammatory disorder. A particular use of an antagonist of OSM is in the manufacture of a medicament to prevent or reduce collagen release from cartilage. The invention further provides a method for the treatment or prophylaxis of an inflammatory arthropathy or inflammatory disorder comprising administering an effective amount of such an antibody which blocks OSM binding to gp130 to a patient suffering from such a disorder.

An antibody of the invention may used in a preparation for the treatment of pro-inflammatory process in which OSM directly or indirectly, such as through the release of inflammatory cytokines, leads to pathogenesis in tissues or organs especially in the skin, lungs, and joints. Such pathologies include osteoarthritis, rheumatoid arthritis, psoriatic arthritis, ankylosing spondylitis, neuropathic arthropathy, reactive arthritis, rotator cuff tear arthropathy, rheumatic fever, Reiter's syndrome, progressive systemic sclerosis, primary biliary cirrhosis, pemphigus, pemphigoid, necrotizing vasculitis, myasthenia gravis, multiple sclerosis, lupus erythematosus, polymyositis, sarcoidosis, granulomatosis, vasculitis, pernicious anemia, CNS inflammatory disorder, antigen-antibody complex mediated diseases, autoimmune haemolytic anemia, Hashimoto's thyroiditis, Graves disease, Reynard's syndrome, glomerulonephritis, dermatomyositis, chronic active hepatitis, celiac disease, autoimmune complications of AIDS, atrophic gastritis, and Addison's disease, endotoxemia or septic shock (sepsis), or one or more of the symptoms of sepsis and other types of acute and chronic inflammation. Those patients who are more particularly able to benefit from the method of the invention are those suffering from infection by *E. coli, Haemophilus influenza B, Neisseria meningitides, staphylococci*, or *pneumococci*. Patients at risk for sepsis include those suffering from burns, wounds, renal or hepatic failure, trauma, burns, immunocompromised (HIV), hematopoietic neoplasias, multiple myeloma, Castleman's disease or cardiac myxoma.

Other conditions that are associated with OSM and amenable to treatment or preventative therapy with the antibodies of the invention include fibrotic disease such as pulmonary fibrosis, diabetic nephropathy, idiopathic pulmonary fibrosis, systemic sclerosis, and cirrhosis. Another indication for use of antibodies of the invention is in the treatment or prevention of nociceptive pain involving neurons of dorsal root ganglia.

Administration and Dosing

The invention provides for stable formulations of an OSM-neutralizing antibody, which is preferably an aqueous phosphate buffered saline or mixed salt solution, as well as preserved solutions and formulations as well as multi-use preserved formulations suitable for pharmaceutical or veterinary use, comprising at least one OSM-neutralizing antibody in a pharmaceutically acceptable formulation. Suitable vehicles and their formulation, inclusive of other human proteins, e.g., human serum albumin, are described, for example, in e.g. Remington: The Science and Practice of Pharmacy, 21st Edition, Troy, D. B. ed., Lipincott Williams and Wilkins, Philadelphia, Pa. 2006, Part 5, Pharmaceutical Manufacturing pp 691-1092, See especially pp. 958-989.

The OSM-neutralizing antibody in either the stable or preserved formulations or solutions described herein, can be administered to a patient in accordance with the present invention via a variety of delivery methods including intravenous (I.V.); intrusclular (I.M.); subcutaneously (S.C.); transdermal; pulmonary; transmucosal; using a formulation in an implant, osmotic pump, cartridge, micropump; or other means appreciated by the skilled artisan, as well-known in the art.

For example, site specific administration may be to body compartment or cavity such as intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, vaginal, rectal, buccal, sublingual, intranasal, or transdermal means.

In general, if administering a systemic dose of the antibody, it is desirable to provide the recipient with a dosage of antibody which is in the range of from about 1 ng/kg-100 ng/kg, 100 ng/kg-500 ng/kg, 500 ng/kg-1 ug/kg, 1 ug/kg-100 ug/kg, 100 ug/kg-500 ug/kg, 500 ug/kg-1 mg/kg, 1 mg/kg-50 mg/kg, 50 mg/kg-100 mg/kg, 100 mg/kg-500 mg/kg (body weight of recipient), although a lower or higher dosage may be administered. Of course, suitable dosages of an antagonist of the present invention will vary, depending upon factors such as the disease or disorder to be treated, the route of administration and the age and weight of the individual to be treated and the nature of the antagonist. Without being bound by any particular dosages, it is believed that for instance for parenteral administration, a daily dosage of from 0.01 to 20 mg/kg of an antibody (or other large molecule) of the present invention (usually present as part of a pharmaceutical composition as indicated above) may be suitable for treating a typical adult.

The treatment may be given in a single dose schedule, or preferably a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

The antibodies of the present invention may be used alone or in combination with immunosuppressive agents such as steroids (prednisone etc.), cyclophosphamide, cyclosporin A or a purine analogue (e.g. methotrexate, 6-mercaptopurine, or the like), or antibodies such as an anti-lymphocyte antigen antibody, an anti-leukocyte antigen antibody, a TNF antagonist e.g. an anti-TNF antibody or TNF inhibitor e.g. soluble TNF receptor, or agents such as NSAIDs or other cytokine inhibitors.

Sequence Table

| SEQ ID NO | Description | SEQUENCE AND FEATURES |
|---|---|---|
| 1 | Human IGHV1-69*01 | QVQLVQSGAE VKKPGSSVKV SCKASGGTFS SYX$_1$ISWVRQA PGQGLEWMGX$_2$ IX$_3$X$_4$X$_5$X$_6$GTANY AQKFQGRVTI TADESTSTAY MELSSLRSED TAVYYCAR<br>Where X$_1$ is A or G, X$_2$ is G or W, X$_3$ may be I or S, X$_4$ may be P or A, X$_5$ may be I or Y and X$_6$ may be F or N. |
| 2 | Human IGHV3-23*01 | EVQLLESGGG LVQPGGSLRL SCAASGFTFS X$_1$YX$_2$MX$_3$WVRQA PGKGLEWVSX$_4$ IX$_5$X$_6$X$_7$GX$_8$STYY ADSVKGRFTI SRDNSKNTLY LQMNSLRAED TAVYYCAK<br>Where X$_1$ may be S, D, N, or T; X$_2$ may be A, G, or W; X$_3$ may be S or H; X$_4$ may by V, A, N or G; X$_5$ may be S, N, K or W; X$_6$ may be Y, S, G, or Q; X$_7$ may be S or D; and X$_8$ may be S or G |
| 3 | Human IGHV5-51*01 | EVQLVQSGAE VKKPGESLKI SCKGSGYSFT X$_1$YWIX$_2$WVRQM PGKGLEWMGX$_3$ IX$_4$PX$_5$DSX$_6$TRY SPSFQGQVTI SADKSISTAY LQWSSLKASD TAMYYCAR<br>Where X$_1$ may be S, N, or T; X$_2$ may be S or G; X$_3$ may be I or R; X$_4$ may by D or Y; X$_5$ may be G or S; X$_6$ may be D or Y |
| 4 | Human JH | WGQGTLVTVSS |
| 5 | Human IGKV1-39*01 (O12) | DIQMTQSPSS LSASVGDRVT ITCRASQSI X$_1$ X$_2$X$_3$LNWYQQKP GKAPKLLIYX$_4$ ASSLQSGVPS RFSGSGSGTD FTLTISSLQP EDFATYYC |

-continued

Sequence Table

| SEQ ID NO: | Description | SEQUENCE AND FEATURES |
|---|---|---|
| | | Where $X_1$ may be A, D, N, S, or R; $X_2$ may be D, G, K, N, or S; $X_3$ may be A, D, F, H, N, S, W, V, or Y; $X_4$ may be A, D, F, G, K, N, T, or Y. |
| 6 | IGKV3-11 (L6) | EIVLTQSPAT LSLSPGERAT LSCRAS<u>QSV $X_1X_2X_3$L</u>AWYQQKP GQAPRLLIY<u>$X_4$</u> <u>ASNRAT</u>GIPA RFSGSGSGTD FTLTISSLEP EDFAVYYC<br>Where $X_1$ may be A, D, N, R or S; $X_2$ may be D, K, N, or S; $X_3$ may be A, D, F, H, N, S, W, or Y; $X_4$ may be A, D, K, G, F, T or N. |
| 7 | Human IGKV3-20 (A27) | EIVLTQSPGT LSLSPGERAT LSC<u>$X_1X_2X_3X_4$</u>SVS <u>SSYLA</u>WYQQK PGQAPRLLIY <u>$X_5$ASSRAT</u>GIP DRFSGSGSGT DFTLTISRLE PEDFAVYYC<br>Where $X_1$ may be D, N, S, R or T; $X_2$ may be N, S, or R; $X_3$ may be A, D, H, N, S, or R; $X_4$ may be E, F, H, K, Q, S, or Y; $X_5$ may be A, D, G, or S. |
| 8 | Human IGKV4-1*01 (B3) | DIVMTQSPDS LAVSLGERAT INC<u>KSSQSVL $X_1$SSNNX$_2$NX$_3$LA</u> WYQQKPGQPP KLLIY<u>$X_4$ASTR</u> <u>ES</u>GVPDRFSG SGSGTDFTLT ISSLQAEDVA VYYC<br>Where $X_1$ may be A, F, H, S, or Y; $X_2$ may be E, K, N, or T; $X_3$ may be A, D, F, H, N, S, W, or Y; $X_4$ may be A, D, S, W or Y. |
| 9 | L-CDR3 formula | QQ$X_1X_2X_3X_4X_5$T<br>Where $X_1$ may be A, D, F, H, P, S, or Y; $X_2$ may be D, E, G, H, I, K, N, R, T or Y; $X_3$ may be D, G, H, K, N, S, T, or R; $X_4$ may be F, I, L, N, R, W or Y as defined in Table 2. |
| 10 | JK4 | FGQGTKVEIK |
| 11 | human OSM protein sequence | <u>AAIGSCSKEYRVLLGQLQKQTDLMQDTSRLLDPYIRIQGLDVPKLR EHCR</u><br><u>ERPGAFPSEETLRGLGRRGFLQTLNATLGCVLHRLADLEQRLPKAQ DLER</u><br><u>SGLNIEDLEKLQMARPNILGLRNNIYCMAQLLDNSDTAEPTKAGRG ASQP</u><br><u>PTPTPASDAFQRKLEGCRFLHGYHRFMHSVGRVFSKWGESPNRSRR HSPH</u><br>QALRKGVRRTRPSRKGKRLMTRGQLPR |
| 12 | Cyno (Macaca fascicularis) OSM protein | AAMGSCSKEYRMLLGQLQKQTDLMQDTSRLLDPYIRIQGLDIPKLR EHCR<br>ESPGAFPSEETLRGLGRRGFLQTLNATLGRVLHRLADLEQHLPKAQ DLER<br>SGLNIEDLEKLQMARPNVLGLRNNIYCMAQLLDNSDMTEPTKAGRG TPQP<br>PTPTPTSDVFQRKLEGCSFLRGYHRFMHSVGRVFSKWGESPNRSRR HSPH<br>QALRKGVRRTRPSRKGNRLMPRGQLPR |
| 13 | H2 H-CDR1 | SYAIS |
| 14 | H14 & H17 H-CDR1 | SYWIS |
| 15 | H135 H-CDR1 | SYWIG |
| 16 | H2 H-CDR2 | GIIPIFGNANYAQKFQG |
| 17 | H14 & H17 H-CDR2 | IIYPGDSYTRYSPSFQG |
| 18 | H135 H-CDR2 | IIYPGDSDTRYSPSFQG |
| 19 | H2 H-CDR3 | YGAKGLLDY |
| 20 | H14 H-CDR3 | GSVFEAYFDY |
| 21 | H17 H-CDR3 | VPVSPAYLDY |

-continued

Sequence Table

| SEQ ID NO: | Description | SEQUENCE AND FEATURES |
|---|---|---|
| 22 | H135 H-CDR3 | GFGASYLDY |
| 23 | B3 & L2 L-CDR1 | KSSQSVLYSSNNKNYLA |
| 24 | L12 L-CDR1 | KSSQSVLSSSNNENWLA |
| 25 | L111 L-CDR1 | KSSQSVLASSNNNNFLA |
| 26 | B3 L-CDR2 | WASTRES |
| 27 | B3 L-CDR3 | QQYYSTPL |
| 28 | L2 L-CDR3 | QQSFSFPI |
| 29 | L-CDR3 consensus | QQ-(SY)-(FY)-S-(FT)-PLT |
| 30 | L171-CDR1 | KSSQSVLSSGNNGNYLA |
| 31 | L172-CDR1 | KSSQSVLSSGSNHNYLA |
| 32 | L173-CDR1 | KSSQSVLSSRGNNNYLA |
| 33 | L174-CDR1 | KSSQSVLGSWGNDNYLA |
| 34 | L175-CDR1 | KSSQSVLYSGGNGNYLA |
| 35 | L176-CDR1 | KSSQSVLGSWGNHYLA |
| 36 | L177-CDR1 | KSSQSVLSSNGNHNYLA |
| 37 | L178-CDR1 | KSSQSVLSSDGNHNYLA |
| 38 | L180-CDR1 | KSSQSVLGSSSNINFLA |
| 39 | L182-CDR1 | KSSQSVLGSGDNRNYLA |
| 40 | L184 & L186 L-CDR1 | KSSQSVLGSGYNRNYLA |
| 41 | L192 L-CDR1 | KSSQSVLGSWHNDNYLA |
| 42 | L-CDR2 | KASTRES |
| 43 | L180-CDR2 | SASTRES |
| 44 | L182-CDR2 | NASTRES |
| 45 | L175-CDR3 | QQYSTTPLT |
| 46 | L180-CDR3 | QQYFSTPIT |
| 47 | Reselected L-CDR3 consensus | QQY-(F, Y)-STP-(L, I)-T |
| 48 | H-FR1-CDR1-FR2-CDR2-FR3 | EVQLVQSGAEVKKPGESLKISCKGSGYSFT<u>SYWIS</u>WVRQMPGKGLE WMG<u>IIYPGDSYTRYSPSFQG</u>QVTISADKSISTAYLQWSSLKASDTA MYYC |
| 49 | L173 | DIVMTQSPDSLAVSLGERATINC<u>KSSQSVLSSRGNNNYLA</u>WYQQKP GQPPKLLIY<u>KASTRES</u>GVPDRFSGSGSGTDFTLTISSLQAEDVAVY YC<u>QQYYSTPL</u> |
| 50 | L178 | DIVMTQSPDSLAVSLGERATINC<u>KSSQSVLSSDGNHNYLA</u>WYQQKP GQPPKLLIY<u>KASTRES</u>GVPDRFSGSGSGTDFTLTISSLQAEDVAVY YC<u>QQYYSTPL</u> |
| 51 | L180 | DIVMTQSPDSLAVSLGERATINC<u>KSSQSVLGSSSNINFLA</u>WYQQKP GQPPKLLIY<u>SASTRES</u>GVPDRFSGSGSGTDFTLTISSLQAEDVAVY YC<u>QQYFSTPI</u> |

-continued

Sequence Table

| SEQ ID NO: | Description | SEQUENCE AND FEATURES |
|---|---|---|
| 52 | L185 | DIVMTQSPDSLAVSLGERATINC<u>KSSQSVLSSGGNWNYLA</u>WYQQKP<br>GQPPKLLIY<u>WASTRES</u>GVPDRFSGSGSGTDFTLTISSLQAEDVAVY<br>YC<u>QQYYTTPL</u> |
| 53 | L186 | DIVMTQSPDSLAVSLGERATINC<u>KSSQSVLSSGSNRNYLA</u>WYQQKP<br>GQPPKLLIY<u>WASTRES</u>GVPDRFSGSGSGTDFTLTISSLQAEDVAVY<br>YC<u>QQYYSTPL</u> |
| 54 | H14 | EVQLVQSGAEVKKPGESLKISCKGSGYSFT<u>SYWIS</u>WVRQMPGKGLE<br>WMG<u>IIYPGDSYTRYSPSFQG</u>QVTISADKSISTAYLQWSSLKASDTA<br>MYYCAR<u>GSVFEAYFDY</u> |
| 55 | H17 | EVQLVQSGAEVKKPGESLKISCKGSGYSFT<u>SYWIS</u>WVRQMPGKGLE<br>WMG<u>IIYPGDSYTRYSPSFQG</u>QVTISADKSISTAYLQWSSLKASDTA<br>MYYCAR<u>VPVSPAYLDY</u> |
| 56 | AviTag | GLNDIFEAQKIEWHE |

The present invention will now be described with reference to the following specific, non-limiting examples.

EXAMPLE 1: REAGENTS AND ASSAYS

In order to select and characterize OSM-binding antibodies, constructs of human and Cyno OSM were generated for mammalian cell expression. Human OSM (NP_065391 encoded by NM_020530) is a 252 amino acid precursor processed into a full-length secreted protein of 227 amino acids (SEQ ID NO: 11), which is a proprotein further processed into the more fully active mature form, amino acids, 1-184. Human OSM cDNA was ordered from OriGene (Cat. No. SC121421) and the ORF of human OSM from the OriGene clone was amplified by PCR and a signal peptide (murine IgG1) was introduced along with a hexa-His tag for protein purification and an AviTag (SEQ ID NO: 56) for site-directed protein biotinylation. The latter was chosen to avoid random chemical biotinylation of lysine residues present in the vicinity of OSM intereaction with receptors.

Cynomolgous monkey OSM was cloned from cyno PBMC's RNA using Superscript III first strand synthesis system (InVitrogen) to obtain the cDNA and then PCR amplified using the UTR primers designed from the human OSM sequence as described in U.S. patent application Ser. No. 12/648,430. The expressed full-length protein is shown in SEQ ID NO: 12 with the cleaved, active form represented by 184 residues, 51-227.

Precursor and mature forms of human and Cyno OSM were expressed in HEK 293 and purified using standard methodologies. The functional activities of the proteins were tested in the A375-S2 cell proliferation and pSTAT3 signaling assays using as control E. coli derived commercially available human OSM (R&D Systems, Cat. No. 295-OM).

Mabs

Where a control antibody was used, a human IgG1 isotype antibody designated CNTO6234 was used.

Chemical Biotinylation

Recombinant human OSM was biotinylated using NHS-ester chemistry (EZ-Link Sulfo-NHS-LC-Biotinylation Kit, Pierce, #21435) targeting amine residues on the cytokine. The biotin-coupling reaction was optimized for a target labeling efficiency of one mole of biotin per mole of antigen. The latter minimizes the loss of binding and functional activity while ensuring near-complete labeling of the protein population. Upon completion of the reaction, the protein was purified from the free biotin reagent and residual leaving groups using Zeba Desalt Spin Columns included in the EZ-Link Sulfo-NHS-LC-Biotinylation Kit (Pierce). Approximately 80% of the starting material was recovered. The HABA assay (Pierce Biotin Quantitation Kit, #28005) was used to measure the level of biotin incorporation, which indicated approximately one mole of biotin per mole of human OSM. An Octet instrument (FortéBIO) was used to verify both streptavidin coupling and gp130-Fc (R&D Systems, Cat. No. 671-GP) binding for the biotinylated protein. Octet measurements showed that biotinylated human OSM bound gp130 with a profile essentially identical to that of the unlabeled starting material.

In Vitro Targeted Biotinylation

The 15 residue AviTag (GLNDIFEAQKIEWHE) (SEQ ID NO: 56) has similar biotin-acceptor kinetics as the endogenous BirA substrate BCCP (Beckett et. al. 1999, Protein Science). When tethered to a protein of interest the AviTag, having one acceptor lysine residue, will be biotinylated at only one position. Recombinant Cyno OSM was biotinylated site-specifically in vitro using biotin-protein ligase and reagents commercially available from Avidity. The biotinylated Cyno OSM was purified using monovalent streptavidin affinity resin. The quality of the resulting protein was assessed by SDS-PAGE and SEC-HPLC. The HABA assay (Pierce Biotin Quantitation Kit, #28005) was used to measure the level of biotin incorporation, which indicated approximately one mole of biotin per mole of cyno OSM. An Octet instrument (FortéBIO) was used to verify both streptavidin coupling and gp130-Fc chimera binding for the biotinylated protein. Octet measurements showed that biotinylated Cyno OSM bound gp130 with a profile essentially identical to that of the unlabeled starting material.

Solid Phase Immunoassays

Initial phage-Fab panning using NEUTRAVIDIN™ ELISA plates (Pierce) coated with 2 µg/ml biotinylated human OSM or cyno OSM in TBS. After overnight incubation at 4° C., blocking and washing, 1:100 dilutions of polyclonal phage pools from each round of panning were added. Bound phage was detected with an HRP-conjugated monoclonal specific for pVIII, the M13 phage major coat protein (GE Healthcare, Cat. No. 27-9421-01), followed by addition of chemiluminescent substrate POD (Roche, Cat. No. 11582950001), and read on a PerkinElmer instrument.

Primary screening of individual clones was performed using secreted soluble Fab-His protein from *E. coli* supernatants. Bacterial supernatants, containing soluble Fab-His protein, were used to carry out binding in an ELISA formats. Black MaxiSorp plates (Nunc, Cat. No. 437111) were coated with 1 pg/ml sheep anti-human Fd (CH1) antibody (The Binding Site, Cat. No. PC075) and incubated at 4° C. overnight. After the plates were washed and blocked, 50 pl undiluted bacterial supernatant (containing Fab-His protein) was added and allowed to incubate for 1 hour at room temperature with gentle shaking. Plates were washed and biotinylated human or Cyno OSM 20 nM was added to the captured Fabs. After 1 hour at room temperature, SA-HRP (Invitrogen, Cat. No. 43-4323) was added and chemiluminescent detection carried out as above. It was calculated that primary binding ELISA screening with human OSM at a concentration of 20 nM would allow the detection of clones with affinities in the nanomolar affinity range.

Epitope Binning

Epitope binning is a competition assay performed in order to group the MAbs on the basis of binding characteristics performed using human IgG1 converted mAbs and the commercial antibody, MAB29, which is known to be an OSMRβ/LIFRα recruitment-blocker (R-blocker).

To each well of a 384-well multi-array plate (Meso Scale Discovery (MSD), L25XA-4) was added 2.5 µg/ml anti-human Fc (Jackson Immuno, 709-005-149) in phosphate buffered saline (PBS) pH7.4 (Sigma, P3813). The plate was incubated at 4° C. overnight then blocked with 50 µl of MSD blocker A at room temperature for 1 hr. The 384 multi-array plate was washed three times (PBS pH7.4, 0.05% Tween 20 (Scytek, PBT010) and to each well was added a 1.0 µg/ml solution of test mAb followed by shaking at level 6 on a titer plate shaker at room temperature for 1 hr. The plate was washed three times as before.

In parallel, a 5 µg/ml solution of a competing mAb and 1 µg/ml biotinylated OSM (R&D Systems, 295-OM-010/CF) were combined in a separate 96-well plate (COSTAR, 3357) in MSD assay buffer (1:3 of block buffer with PBS pH7.4, 0.05% Tween 20) and shaken at level 3 on a titer plate shaker at room temperature for 1 hr. The pre-complex of competing antibody and biotinylated OSM was added to each well of the 384 multi-array plate and shaken (level 6 on a titer plate shaker) at room temperature for 1 hr. The plate was washed three times and to each well was added streptavidin sulfo TAG (MSD, R32Ad-S) and shaken (level 6 on a titer plate shaker) at room temperature for 30 min. The plate was washed three times and to each well was added read buffer T diluted 1:4 with distilled water (MSD, R92TC-1). The plate was read on an MSD 56000 instrument.

The data was interpreted on the basis of the signal attained for a test mAb in the presence of biotinylated OSM with no competing mAb present (maximum signal) together with the signal from self competition (2-4 fold reduction in maximum signal). Epitope competition was assigned when the value in the presence of a competing mAb was within three standard deviations of the value of that from self competition.

A375 Cells

A375 cells (ATCC; CRL-1619) are a human epithelia cell derived from malignant melanoma. A375-S2 cells (ATCC; CRL-1872, a subline of CRL-1619 sensitive to IL-1) are cultured in complete growth medium (DMEM/GlutaMax-I, Gibco) supplemented with 10% FBS (Gibco) in T-175 culture flasks (Corning; Cat. No. 431080) and sub-cultured when approximately 80% confluent every three to four days in a 1:20 sub-culture ratio.

A375-S2 Cell Proliferation (BrdU-Incorporation) Assay

The reduction in A375-S2 cells proliferation by human or Cynomolgus monkey OSM was measured by BrdU-incorporation using a chemiluminescent ELISA. Oncostatin M reduces proliferation in the A375-S2 human melanoma cell line (Zarling et al. PNAS 83:9739-9743). This cell line was used to evaluate the anti-oncostatin M antibodies at all stages of antibody discovery. A375-S2 cells were maintained in T-150 tissue culture flasks (BD Falcon 35-5001) in DMEM (Gibco 11995)+10% FBS (Gibco 16140)+1% Pen/Strep (Gibco 15140) at 37° C. in 95% O2-5% CO2 and split 1:10 twice per week.

To perform the proliferation assay, cells were trypsinized (0.25%, Gibco 25200) to remove them from the T150 flasks and then plated at a density of 2000 cells/well in the inner 48 wells of black TC-coated plates (BD Falcon 353948) in 200 µL of DMEM/FBS/Pen-Strep. After overnight incubation at 37° C./95% O2-5% CO2, the media was removed and replaced with 180 µL of fresh media. A separate plate was prepared which contained all of the test solutions at 10× the final concentrations. From this plate, 20 µL was transferred to the corresponding well in the cell plate to generate the appropriate experimental conditions. Each experimental condition was tested in triplicate. In any experiment which evaluated neutralization, the antibody and Oncostatin M were incubated together for at least 1 hour being added to cells. The plates were then incubated at 37° C./95% O2-5% CO2 for an additional 72 hours. At this time the Chemiluminescent BrdU Cell Proliferation ELISA (Roche 11669915001) was performed. The BrdU labeling reagent was added to the culture for 4 hours. The media was then removed, and 100 µL of fix solution was added to each well. After 30 min at room temperature the solution was removed and 100 µL/well of anti-BrdU-POD solution was added. After 2 hours at room temperature, the plate was washed with PBS-Tween and 100 µL of Super Signal Pico (Thermo Scientific 37069) was added to each well. Luminescence was then read using a Perkin Elmer Victor3 instrument.

Initial experiments were done to determine the dose-response of the in-house generated CHO cell-derived recombinant human and cynomolgous monkey oncostatin M in suppressing proliferation. Osm was tested from a starting concentration of 100 ng/ml with 1 to 5 dilutions to a final concentration of 0.0244 ng/ml. Percent inhibition of proliferation was calculated compared to cells treated with vehicle control. The results of such an experiment are shown in FIG. 2A. As the concentration of human or cyno Oncostatin M is increased there is a corresponding reduction in BrdU incorporation. The antiproliferative activity of human and cynomolgous monkey Oncostatin M is indistinguishable, based on both the extent of anti-proliferative activity and on the EC50 of the effect.

Based on these experiments, a concentration of 2 ng/ml of Oncostastin M was used to evaluate and compare anti-Oncostatin M antibodies because this concentration inhibited proliferation approximately 80%, giving a large window in which to determine antibody dose responses. A full dose-range of antibody was evaluated in the presence of 2 ng/ml of human or cyno Oncostatin M. In addition, an isotype control was included in the experiment at the highest concentration of anti-Oncostatin M antibody used. The assay window was defined by the difference between untreated control wells (maximum proliferation) and wells incubated with 2 ng/ml Oncostatin M alone (minimum proliferation) and the percent neutralization at any concentration of antibody was defined within this window.

pSTAT3 Signaling Using A375-S2 Phospho-STAT3Assay

OSM inhibits the growth of A375-S2 cells by binding cell surface receptor gp130 and inducing receptor heterodimerization with OSMlZO to initiate an intracellular signaling cascade that includes activation (phosphorylation) of the signaling molecule STAT3 (Kortylewski et al., Oncogene 18: 3742-3753, 1999). Disruption of STAT3 signaling abolishes OSM growth inhibition of A375-S2 cells, demonstrating that STAT3 activation is a key step in OSM signaling (Heinrich et al., Biochem. J. 374: 1-20, 2003). STAT3 phosphorylation in A375-S2 cells has been shown to be OSM concentration dependent and commercial kits are available to measure it in stimulated cells. Neutralization of OSM-induced STAT3 phosphorylation in A375-S2 cells was chosen as a primary screening assay for Mabs candidates.

For antibody neutralization of OSM-induced STAT3 phosphorylation A375-S2 cells are seeded into 96-well tissue culture plates (Corning; Cat. No. 3596) at 25,000 cells/well in 200 µl in complete growth media and incubated for 24 hours. Cells are treated with a solution containing 5 ng/ml human OSM (recombinant, mammalian-cell derived, OSMN1-1) which has been pre-incubated for 3 hours at room temperature with 1:5 serially diluted experimental mAb starting at 10 µg/ml. Controls include untreated cells, stimulated cells (5 ng/ml OSM only) and a hIgG1 isotype control mAb. All treatments are performed in triplicate unless otherwise noted.

Analysis of pSTAT3 content is carried out using the Phospho-STAT3 Whole-Cell Lysate Kit (MSD; Cat. No. K150DID-1, Lot No. K0010570) following the manufacturer's protocol. Briefly, the cells are treated in a 200 µl/well volume for 10 minutes; treatment solutions are removed and 50 µl of cell MSD lysis buffer is added via multichannel pipette. The plate is placed on an orbital shaker (at 300 RPM) for 5 minutes. Thereafter, 30 µl of each lysate is transferred to the MSD phospho-STAT3 96-well plate. The plate is sealed and placed on an orbital shaker (at 300 RPM) for 1 h at room temperature, washed three times with 150 µl of MSD wash buffer, and 25 µl of secondary detection antibody conjugate (anti-pSTAT3-Ru(bpy)32+) added to each well, again sealed and incubated on an orbital shaker (at 300 RPM) for 1 h at room temperature. The plate is washed as previously and 150 µl of MSD read buffer (tripropylamine solution) is added to each well. The plate is read on an MSD SECTOR Imager 6000 instrument.

Full EC50 dose-response curves for inline matured, parental and control mAbs were obtained and plotted as normalized percent pSTAT3 signal.

Affinity Measurement by Surface Plasmon Resonance (Biacore)

The binding affinities were measured using Surface Plasmon Resonance (SPR) with a Biacore 3000 optical biosensor (Biacore) using human or Cyno OSM constructs as described. A biosensor surface was prepared by coupling anti-IgG Fc antibody mixture of anti-Mouse (Jackson, Cat. No. 315-005-046) and anti-Human (Jackson, Cat. No. 109-005-098) to the carboxymethylated dextran surface of a CM-5 chip (Biacore, Cat. No. BR-1000-14) using the manufacturer's instructions for amine-coupling chemistry. Approximately 19,000 RU (response units) of anti-OSM antibody were immobilized in each of four flow cells. The kinetic experiments were performed at 25° C. in running buffer (DPBS+0.005% P20+3 mM EDTA). Serial dilutions Human and Cyno OSM ECD from 100 nM to 0.412 nM were prepared in running buffer. About 200 RU of mAb were captured on flow cells 2 to 4 of the sensor chip. Flow cell 1 was used as reference surface. Capture of mAb was followed by a three-minute injection (association phase) of antigen at 50 µl/min, followed by 10 minutes of buffer flow (dissociation phase). The chip surface was regenerated by two pulses of 18-second injections of 100 mM H3PO4 (Sigma, Cat. No. 7961) at 50 µl/min.

The collected data was processed using the BlAevaluation software (Biacore, version 3.2). First, double reference subtraction of the data was performed by subtracting the curves generated by buffer injection from the reference-subtracted curves for analyte injections. Kinetic analysis of the data was performed using 1:1 binding model with global fit. The result for each mAb was reported in the format of Ka (On-rate), Kd (Off-rate) and $K_D$ (affinity constant).

EXAMPLE 2: SELECTION OF OSM BINDING FABS

The de novo Fab-pIX libraries have been described Shi et al. J Mol Biol 397:385-396, 2010; WO09085462A1; U.S. Ser. No. 12/546,850; and herein above are designated 169, 323 and 551 which references the heavy-chain human germline framework being used: IGHV1-69 (SEQ ID NO: 1), IGHV3-23 (SEQ ID NO: 2), or IGHV5-51(SEQ ID NO: 3) in IMGT nomenclature. The three heavy-chain library frameworks are combined with four light-chain library $VL_{kappa}$ frameworks: A27 (IGKV3-20*01 (SEQ ID NO: 5)), B3 (IGKV4-1*01 (SEQ ID NO: 6), L6 (IGKV3-11*01 (SEQ ID NO: 7)), and O12 (IGKV1-39*01 (SEQ ID NO: 8)). In the libraries, the Fabs V-regions are completed by the addition of a J-region (FR4) comprising SEQ ID NO: 4 in the heavy chains and SEQ ID NO: 10 in the light chains. The heavy chain CDR3 is of variable length from 7-14 residues. Examples of the complete V-regions for each library are shown in FIG. 1 and numbered and CDR regions shown according to Kabat.

The initial set of anti-OSM phage display hits were identified using commercially available aglycosylated human OSM. The Fab-pIX phage display libraries were panned using biotinylated human OSM (R&D Systems, Cat. No. 295-OM) capture on paramagnetic Streptavidin (SA) beads (Invitrogen, Cat. No. 112.05D) following a published protocol for phage selection (Marks and Bradbury, Antibody Engineering, Vol. 248: 161-176, Humana Press, 2004). Briefly, biotinylated human OSM was added to the phage libraries that had been pre-absorbed on unconjugated beads, to a final concentration of 100 nM and incubated for 1 hour with gentle rotation. Blocked SA beads were added and incubated for 15 minutes to capture biotinylated OSM with bound phage. The magnetically-captured phage/antigen/bead complex was washed 5 times with 1 ml of TBST and once with 1 ml TBS. Following removal of the final TBS wash, 1 ml of exponentially growing TG1 cells (Stratagene, Cat. No. 200123) was added and incubated at 37° C. for 30 minutes without shaking. Infected bacteria were spread on LB/Agar (1% Glucose/100 µg/ml Carbenicillin) plates (Teknova, Cat. No. L5804) and incubated overnight at 37° C. Bacterial lawns were scraped and glycerol stocks prepared [15% glycerol/Carbenicillin (100 µg/ml)/2xYT] and stored at –80° C. To prepare phage for second-round panning, 25 ml of 2xYT/Carbenicillin (100 µg/ml) was inoculated with 25 µl of bacterial glycerol stock and grown at 37° C. until an OD600 of roughly 0.5. Helper phage VCSM13 (Stratagene, Cat. No. 200251) was added to the culture at a multiplicity of infection of approximately 10:1 and incubation was carried out for 30 minutes at 37° C. without shaking. The bacteria was spun down and the pellet resuspended in induction media (2xYT/Carb/Kan/IPTG) and grown at 30° C. overnight. Phage was precipitated with 2% PEG/0.25 M NaCl (final concentrations) and re-suspended in 2 ml of PBS. First-round phage was stored at 4° C. and used to carry out second-round panning. The panning parameters were: Round 1, 100 nM antigen, 1 hour incubation at room temperature, 5× washes with TBST followed by 1× wash with TBS; Round 2, 10 nM antigen, 1 hour incubation at room temperature, 10× washes with TBST/1× wash with TBS; and Round 3, 1 nM antigen, 16 hour (overnight) incubation at 4° C., 10× washes with TBST/1× wash with TBS.

Success was monitored using an ELISA where Fabs were captured with an anti-human Fd (CH1) antibody and biotinylated human OSM was added at 20 nM and bound OSM was detected with SA-HRP.

Thirty (30) unique heavy chain-light chain pairings as displayed Fabs were identified that were shown to cross react with Cyno OSM by ELISA. The heavy chains represented sequences from the 169 (IGHV1-69 derived) and 551 (IGHV5-51 derived) libraries and were combined with light chain variable regions representing all four of the library germline origins (A27, B3, L6, and O12).

EXAMPLE 3: CHARACTERIZATION OF OSM BINDING MABS

The four-helix bundle architecture OSM is characterized by four α helical segments designated A, B, C and D linked by relatively unstructured loops. OSM interacts with gp130 via an surface located in helices A and C (Site II) which was determined to include contact by amino acid residues Q16, Q20, G120, N123, N124 of SEQ ID NO: 1 (Deller et al. Structure 8(8): 863-874, 2000; Liu et al. Int. J. Mol. Med. 23: 161-172, 2009). The surface responsible for OSM interaction with OSMRβ and LIFRα (Site III) is believed to be largely defined by residues located in helix D (Deller et al. ibid).

It was the objective to select high affinity binders to OSM capable of preventing OSM driven gp130 signaling either through the prevention of OSM binding to gp130 (Site II or B-blocker) or prevention of OSM bound gp130 recruitment of the LIFRα or OSMRb (Site III or R-blocker).

Of the 30 initially selected OSM-binding Fabs, 29 were cloned into vectors for conversion to full-length human IgG1 Mabs. The characterization assays were (1) competitive binding to identify epitope groups or "bins", (2) affinity measurements by surface Plasmon resonance (Biacore), and (3) ability to block pSTAT3 signaling. All screens and assays have been carried out using the mammalian cell produced (glycosylated) human and cyno proteins as described in Example 1.

Results

The data for the affinity measurements for a subset of the mAbs selected on the basis of their ranking relative to control MAB295 (R&D Systems) in the pSTAT3 and ELISA binding assays is shown in Table 3.

TABLE 3

Affinity of select subset of anti-OSM first round mAbs.

| mAb | Binding to Human OSM | | | Binding to cyno OSM | | | $K_D$ ratio |
| | ka (1/Ms) $10^4$ | kd (1/s) $10^{-4}$ | KD (nM) | ka (1/Ms) $10^4$ | kd (1/s) $10^{-4}$ | KD (nM) | Cyno/ Human |
|---|---|---|---|---|---|---|---|
| MAB295 | 118.00 | 21.70 | 1.85 | 70.95 | 141.00 | 19.75 | 10.70 |
| M2 | 54.57 | 9.03 | 1.66 | 50.23 | 67.40 | 13.50 | 8.10 |
| M6 | 19.15 | 1.97 | 1.03 | 20.30 | 2.99 | 1.48 | 1.40 |
| M22 | 10.20 | 3.57 | 3.52 | 9.43 | 101.00 | 107.00 | 30.40 |
| M9 | 6.63 | 0.81 | 1.22 | 7.31 | 0.54 | 0.73 | 0.60 |
| M21 | 30.00 | 12.55 | 4.17 | 31.80 | 14.30 | 4.50 | 1.10 |
| M10 | 6.02 | 0.63 | 1.05 | 5.33 | 10.05 | 18.90 | 18.10 |
| M7 | 8.24 | 1.08 | 1.31 | 8.49 | 0.37 | 0.43 | 0.30 |
| M3 | 39.85 | 1.75 | 0.44 | 41.95 | 1.20 | 0.29 | 0.70 |
| M19 | 7.89 | 0.26 | 0.34 | 7.70 | 2.43 | 3.15 | 9.40 |
| M25 | 8.19 | 5.09 | 6.21 | 9.45 | 71.70 | 75.80 | 12.20 |
| M24 | | | Weak | | | No Binding | NA |
| M8 | 4.71 | 0.33 | 0.70 | 4.98 | 0.31 | 0.62 | 0.90 |
| M4 | | | Weak | | | Weak | NA |
| M20 | 16.60 | 7.43 | 4.48 | 15.30 | 16.20 | 10.60 | 2.40 |
| M5 | 6.59 | 7.79 | 11.85 | 9.22 | 11.10 | 12.05 | 1.00 |
| M17 | 2.78 | 0.45 | 1.61 | 2.90 | 0.77 | 2.64 | 1.60 |
| M11 | 8.64 | 8.32 | 9.63 | 19.65 | 10.70 | 5.46 | 0.60 |
| M27 | 6.39 | 34.95 | 55.50 | | | Weak | NA |
| M18 | | | Weak | | | No binding | NA |

The results of the binning assay showed that M5, M6 and M9 competed with each other but not with MAB295. M10 did compete with MAB295. These four mAbs were also shown by the pSTAT3 assay to be functional neutralizers of gp130 signaling. Therefore, it follows that M10 is a R-blocker and that M5, M6 and M9 block OSM binding to gp130 (B-blockers).

The target affinity for a therapeutic lead was dictated by the need to compete decisively the OSM-gp130 interaction whose affinity ($K_D$) has been measured to be approximately 1 nM. Therefore, a target affinity for OSM of 100 pM or lower $K_D$ was desired.

Neutralizing MAbs M5, M6 and M9, found to be OSM-gp130 interaction blockers, plus M10 were chosen for inline maturation in order to produce derivates that met the 100 pM affinity requirement for a therapeutic candidate. It was an additional desired property that mAbs bind cynomolgus monkey OSM with an affinity within fivefold that for human OSM ($K_D$ of 500 pM or less).

The compositions of the binding domains for these four Mabs were found to represent four unique heavy and light chain pairs designated as shown in Table 4.

TABLE 4

| Mab | HC Library | HC ID | LC ID |
|-----|-----------|-------|-------|
| M10 | 169 | H2 | L2 |
| M6 | 551 | H14 | L12 |
| M9 | 551 | H17 | IGKV4-1 (B3) |
| M5 | 551 | H135 | L111 |

The complete variable region sequences comprise the germline sequences used to create the phage library as described herein above and, therefore, the fixed residues match the unmutated parent germline residues. As such, each V-region is comprised of the designated CDR1 and CDR2 within the scaffold designated as SEQ ID NO: 1-3 or 5-8; followed by CDR3 (Table 3 and 4) and for the light chain variable region, respectively (Table 5 for LC and Table 6 for the HC) followed by a J-region as SEQ ID NO: 4 for the heavy chain and SEQ ID NO: 10 for the light chain.

TABLE 5

| VH ID | Framework (SEQ ID NO:) | H-CDR1 | SEQ ID NO: | H-CDR2 | SEQ ID NO: | H-CDR3 | SEQ ID NO: |
|-------|-----|------|-----|------|-----|------|-----|
| H2 | 1-69 (1) | SYAIS | 13 | GIIPIFGNANYA QKFQG | 16 | YGAKGLLDY | 19 |
| H14 | 5-51 (3) | SYWIS | 14 | IIYPGDSYTRYS PSFQG | 17 | GSVFEAYFDY | 20 |
| H17 | 5-51 (3) | SYWIS | 14 | IIYPGDSYTRYS PSFQG | 17 | VPVSPAYLDY | 21 |
| H135 | 5-51 (3) | SYWIG | 15 | IIYPGDSDTRYS PSFQG | 18 | GFGASYLDY | 22 |

The HC variable region H2 comprises the FR1-CDR1-FR2-CDR2-FR3 derived from SEQ ID NO: 1 where $X_1$=A, $X_2$=G, $X_3$=I, $X_4$=P, X5=I, and $X_6$=F with an additional mutation in H-CDR2. The HC from library 551 (H14, H17, and H135) comprise FR1-CDR1-FR2-CDR2-FR3 derived from SEQ ID NO: 3 where, $X_1$=S, $X_2$ S or G, $X_3$=$X_4$=Y, $X_5$=G and $X_6$=Y or D. Each of the four HC were comprised of a unique CDR3 (SEQ ID NOS: 19-22).

TABLE 6

| VL ID | Framework (SEQ ID NO:) | CDR1 | SEQ ID NO: | CDR2 | SEQ ID NO: | CDR3 | SEQ ID NO: |
|-------|-----|------|-----|------|-----|------|-----|
| IGKV4-1 (B3) | B3 (8) | KSSQSVLYSSN NKNYLA | 23 | WASTRES | 26 | QQYYSTPL | 27 |
| L2 | B3 (8) | KSSQSVLYSSN NKNYLA | 23 | WASTRES | 26 | QQSFSFPI | 28 |
| L12 | B3 (8) | KSSQSVLSSSN NENWLA | 24 | WASTRES | 26 | QQYYSTPL | 27 |
| L111 | B3 (8) | KSSQSVLASSN NNNFLA | 25 | WASTRES | 26 | QQYYSTPL | 27 |

The LC variable regions of the selected Fabs all derive from the B3 library and include the curated germline sequence represented in the IMGT database as IGKV4-1 (B3) which was used as a starting sequence for the library diversification as described herein and referenced publications. Three of the four light chains had differences in CDR1 and had identical H-CDR2. A consensus sequence for the four selected LC variable FR1-CDR1-FR2-CDR2-FR3 derived from SEQ ID NO: 8 wherein $X_1$ is Y, S, or A; $X_2$ is K, E, or N; $X_3$ is Y, W or F; and $X_4$ is always W.

Two unique CDR3 sequences were identified. The L-CDR3 can be represented by a consensus sequence (SEQ ID NO: 29) represented by the formula Q-Q-(S,Y)-(F,Y)-S-(F,T)-PLT.

EXAMPLE 4. AFFINITY RESELECTION

The four V-region pairings, OSMM5, OSMM6, OSMM9 and OSMM10, described in Example 3 were chosen for light chain reselection in order to improve affinity. To affinity mature large numbers of antibodies from primary selections in an efficient and expeditious manner, an "in-line" maturation process described in Shi et al. J Mol Biol 397:385-396, 2010 and WO09085462A1 and U.S. Ser. No. 12/546,850 was used. In brief, the $V_H$ regions of antigen-specific clones obtained in initial rounds of selection were combined with libraries of the corresponding $V_L$ scaffold, in this case the B3 based V-region (SEQ ID NO: 8).

Three new libraries were created, one using the $V_L$ library used in the primary selections as source of diverse $V_L$ chains, and two additional libraries designed based on a recent analysis of the antigen-antibody complexes of known structure (Raghuanthan et al., J. Mol. Recognit, 2010). Residues were selected for diversification based on those residues most likely to be involved in the binding of the target protein also called specificity determining residue usage (SDRU). In the Vkappa light chains this has been determined to be three regions of contacts centered around the hypervariable loops as defined by Chothia and Lesk which differ slightly depending upon whether the target is a protein, a peptide, or a small hapten. Table 5 shows the $V_L$ libraries used for affinity maturation, where B3 is the same library used during the discovery phase, Library 2 "SDRM focused" is based on the SDRU residues and focused diversity, and NNK is a randomized library. In the table, "X" means any amino acid plus one stop codon generated by a NNK mix.

Table 7 summarizes the diversity in Libraries 1, 2 and 3. During anlaysis of the final library, some amino acids were identified that were not part of the original design and thus were introduced as a consequence of the synthesis method. For library 2, synthesized using dinucleotides, these amino acids were: S (position 30c), T (position 30d), EK (position 30f), IW (position 32), TV (position 50), I (position 92), D (position 93), and F (position 96).

TABLE 7

| CDR | Position Sequential | Kabat | Library 1 pIX B3 de novo | 2 SDRM focused | 3 SDRM NNK |
|---|---|---|---|---|---|
| L1 | 30 | 30 | L | L | L |
|  | 31 | 30a | YSHFA | RNDGHSY | X |
|  | 32 | 30b | S | S | S |
|  | 33 | 30c | S | RNDGHWSY | X |
|  | 34 | 30d | N | RNDGHSTY | X |
|  | 35 | 30e | N | N | N |
|  | 36 | 30f | KTNE | EKRNDGHWY | X |
|  | 37 | 31 | N | N | N |
|  | 38 | 32 | YFHNWDAS | IRNDWY | X |
| L2 | 56 | 50 | WSRDYA | YWNKTV | X |
| L3 | 97 | 91 | YSHA | SYGH | X |

Fab-His protein was prepared from third-round panning outputs and monoclonal Fab-His ELISAs employed to identify individual hits with higher binding signal than the corresponding parental Fab. Two concentrations of biotinylated human antigen were used in these ranking ELISAs: 2 nM and 0.2 nM. The binding signal for each parental clone was set as 100%. There were 22 hits from the affinity maturation of M6 and M9 showing up to a 9-fold (900%) improved binding when compared to the parental Fab comprising the original heavy and light chain V-regions. Some of these new pairings of heavy and light chains were chosen for further evaluation.

The affinity ($K_D$) of inline matured mAbs for human and cynomolgus monkey OSM compared to that of MAB295 control and parental mAbs M6 and M9 are summarized in Table 8 and the CDR composition of those mAbs shown in Table 9. In some cases, a LCV was paired with both H14 and H17. Certain mAbs that were designated candidate therapeutic leads on the basis of their biophysical properties and functional potencies are highlighted in gray.

TABLE 8

| In-line Matured Anti-OSM mAbs | | | Affinity for Human OSM | | | Affinity for Cyno OSM | | | |
|---|---|---|---|---|---|---|---|---|---|
| mAb | Heavy Chain ID | Light Chain ID | On-rate ka (1/Ms) 10^4 | Off-rate kd (1/s) 10^-4 | Affinity KD (nM) | On-rate ka (1/Ms) 10^4 | Off-rate kd (1/s) 10^-4 | Affinity KD (nM) | Cyno/Human Ratio |
| MAB295 | | | 11.80 | 2.17 | 1.85 | 7.10 | 14.10 | 19.75 | 10.70 |
| M5 | H14 | L12 | 1.68 | 21.20 | 1.260 | 1.85 | 30.70 | 1.660 | 1.3 |
| M42 | H14 | L173 | 2.88 | 13.90 | 0.484 | 2.65 | 13.70 | 0.516 | 1.1 |
| M45 | H14 | L176 | 4.68 | 6.73 | 0.144 | 3.80 | 6.03 | 0.159 | 1.1 |
| M53 | H14 | L184 | 1.83 | 3.92 | 0.214 | 1.84 | 2.71 | 0.147 | 0.7 |
| M54 | H14 | L185 | 3.20 | 1.70 | 0.053 | 3.51 | 2.01 | 0.057 | 1.1 |
| M55 | H14 | L186 | 3.51 | 1.90 | 0.054 | 3.86 | 2.22 | 0.058 | 1.1 |
| M9 | H17 | B3 | 0.60 | 8.54 | 1.420 | 0.65 | 5.83 | 0.898 | 0.6 |
| M62 | H17 | L171 | 2.62 | 4.82 | 0.184 | 2.85 | 6.19 | 0.217 | 1.2 |
| M63 | H17 | L172 | 4.22 | 4.89 | 0.116 | 4.50 | 4.36 | 0.097 | 0.8 |
| M64 | H17 | L173 | 3.15 | 2.98 | 0.095 | 3.29 | 0.75 | 0.023 | 0.2 |
| M65 | H17 | L174 | 8.59 | 5.45 | 0.064 | 6.42 | 3.40 | 0.053 | 0.8 |
| M66 | H17 | L175 | 3.20 | 2.29 | 0.071 | 3.73 | 4.59 | 0.124 | 1.7 |
| M67 | H17 | L176 | 6.40 | 3.39 | 0.053 | 5.24 | 1.80 | 0.034 | 0.6 |
| M68 | H17 | L177 | 3.43 | 2.55 | 0.064 | 4.35 | 2.12 | 0.049 | 0.8 |
| M69 | H17 | L178 | 3.75 | 1.83 | 0.045 | 4.84 | 2.99 | 0.062 | 1.4 |
| M71 | H17 | L180 | 3.44 | 3.61 | 0.105 | 4.09 | 4.42 | 0.108 | 1.0 |
| M83 | H17 | L192 | 4.66 | 1.94 | 0.042 | 4.67 | 1.39 | 0.030 | 0.7 |

TABLE 7-continued

| CDR | Position Sequential | Kabat | Library 1 pIX B3 de novo | 2 SDRM focused | 3 SDRM NNK |
|---|---|---|---|---|---|
|  | 98 | 92 | YNDSHIFKG | ISYGN | X |
|  | 99 | 93 | SNTDGHR | DSTER | X |
|  | 100 | 94 | TYLVFAS | YSHT | X |
|  | 102 | 96 | WYFLIR | FYRWL | X |

TABLE 9

LC-CDR Table for Higher Affinity Mabs

| PAIRED VH ID | VL ID | L-CDR1 | SEQ ID NO: | L-CDR2 | SEQ ID NO: | L-CDR3 | SEQ ID NO: |
|---|---|---|---|---|---|---|---|
| H17 | IGKV4-1(B3) | KSSQSVLYSSNNKNYLA | 23 | WASTRES | 26 | QQYYSTPLT | 27 |
| H14 | L12 | KSSQSVLSSSNNENWLA | 24 | WASTRES | 26 | QQYYSTPLT | 27 |
| H17 | L171 | KSSQSVLSSGNNGNYLA | 30 | KASTRES | 42 | QQYYSTPLT | 27 |
| H17 | L172 | KSSQSVLSSGSNHNYLA | 31 | KASTRES | 42 | QQYYSTPLT | 27 |

TABLE 9-continued

LC-CDR Table for Higher Affinity Mabs

| PAIRED VH ID | VL ID | L-CDR1 | SEQ ID NO: | L-CDR2 | SEQ ID NO: | L-CDR3 | SEQ ID NO: |
|---|---|---|---|---|---|---|---|
| H14/7 | L173 | KSSQSVLSSRGNNNYLA | 32 | KASTRES | 42 | QQYYSTPLT | 27 |
| H17 | L174 | KSSQSVLGSWGNDNYLA | 33 | KASTRES | 42 | QQYYSTPLT | 27 |
| H17 | L175 | KSSQSVLYSGGNGNYLA | 34 | KASTRES | 42 | QQYSTTPLT | 45 |
| H14/7 | L176 | KSSQSVLGSWGNGHYLA | 35 | KASTRES | 42 | QQYYSTPLT | 27 |
| H17 | L177 | KSSQSVLSSNGNHNYLA | 36 | KASTRES | 42 | QQYYSTPLT | 27 |
| H17 | L178 | KSSQSVLSSDGNHNYLA | 37 | KASTRES | 42 | QQYYSTPLT | 27 |
| H17 | L180 | KSSQSVLGSSSNINFLA | 38 | SASTRES | 43 | QQYFSTPIT | 46 |
| H14 | L182 | KSSQSVLGSGDNRNYLA | 39 | NASTRES | 44 | QQYYSTPLT | 27 |
| H14 | L186 | KSSQSVLGSGYNRNYLA | 40 | KASTRES | 42 | QQYYSTPLT | 27 |
| H14 | L184 | KSSQSVLGSGYNRNYLA | 40 | WASTRES | 26 | QQYYSTPLT | 27 |
| H17 | L192 | KSSQSVLGSWHNDNYLA | 41 | KASTRES | 42 | QQYYSTPLT | 27 |

The LC-CDR3 diversity Q-Q-(S,Y)-(F,Y)-S-(F,T)-PLT (SEQ ID NO: 29) in the selected candidates was reduced, and the consensus sequence for the re-selected high affinity LC-CDR3 is represented as QQY-(F,Y)-STP-(L,I)-T (SEQ ID NO: 47).

For the re-selected mAbs, the VH of H14 and H17 share a common FR1-CDR1-FR2-CDR2-FR3 which is given by SEQ ID NO: 48 and comprising SEQ ID NO: 14 (CDR1) and SEQ ID NO: 17 (CDR2).

Ability to Reduce Human and Cyno A375-S2 Cell proliferation

Figure 2B:
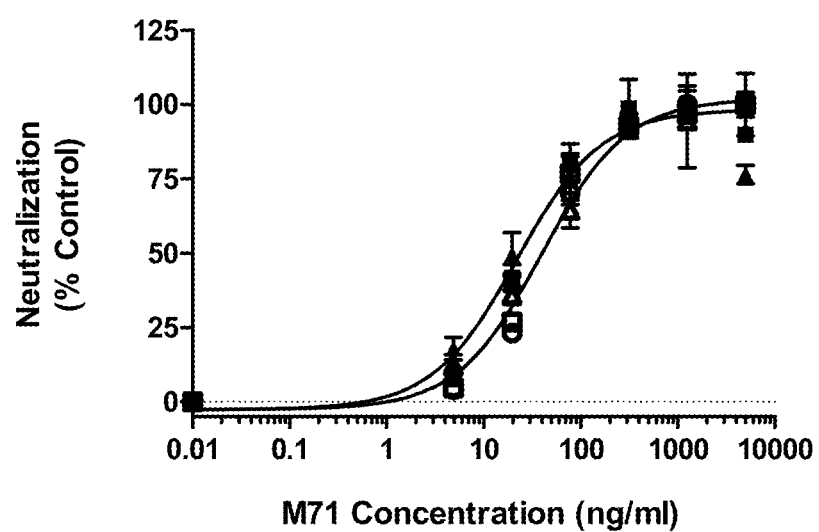
FIG. 2B is a graph showing the ability of the antibody M71, comprised of the L180 (SEQ ID NO: 53) and H17 (SEQ ID NO: 54) variable domains to relieve OSM suppression of A375-S2 proliferation where OSM was present at a concentration of 2 ng/ml.

To evaluate the in-line matured antibodies, dose-responses were conducted starting at 5 µg/ml or 1 µg/ml with 1 to 5 dilutions down to 0.0016 or 0.00032 µg/ml, respectively. Neutralization by M71 is shown in FIG. 2B. As the concentration of the antibody is increased, the anti-proliferative effect of both human and cynomolgous monkey Oncostatin M is neutralized. The dose-response curves were calculated using data from three separate experiments with human (open symbols) and cynomologous monkey (closed symbols) Oncostatin M. Table 10 summarizes the $IC_{50}$ (with 95% confidence intervals) of M55, M64, M69 and M71 against human and cynomolgous monkey Oncostatin M.

TABLE 10

| | Human OSM | | Cyno OSM | |
|---|---|---|---|---|
| Antibody | $IC_{50}$ (ng/ml) | 95% C.I. | $IC_{50}$ (ng/ml) | 95% C.I. |
| M55 | 54.5 | 42.5 to 70.0 | 88.4 | 67.8 to 115.2 |
| M64 | 162.4 | 125.7 to 210 | 321.1 | 272.6 to 378.1 |
| M69 | 44.6 | 32.7 to 60.9 | 50.81 | 37.4 to 69.1 |
| M71 | 21.9 | 16.9 to 28.4 | 39.67 | 31.2 to 50.4 |

Human gp130 Competition

Competition experiments were carried out between the anti-OSM mAbs chosen for inline maturation plus the selected new binders from the table above and Human gp130 using Surface Plasmon Resonance (SPR) with a Biacore 3000 optical biosensor (Biacore) as described in Example 1.

The biosensor surface was prepared by coupling each test mAb to the carboxymethylated dextran surface of a CM-5 chip (Biacore, Cat# BR-1000-14) following the manufacturer's instructions. Approximately 4,000-15,000 RU (response units) of each test mAb were immobilized in one the instrument's four flow cells. Competition experiments were performed at 25° C. in running buffer (DPBS+0.005% P20+3 mM EDTA). Human OSM (in-house, OSMN1-1) was diluted to 30 nM in running buffer and injected at 3 µl/min for 3 minutes over each of the flow cells with immobilized mAb. Following human OSM capture there was a three-minute injection (association phase) of either a competing mAb or human gp130-Fc at 300 nM followed by buffer flow (dissociation phase) for 3 minutes. The chip surface was regenerated by two 12-second pulses of 100 mM $H_3PO_4$ (Sigma, Cat#7961) at 50 µl/min. The collected data were processed using BIAevaluation software version 3.2 (Biacore). First, the sensorgrams were aligned upon injection of human OSM. Then the binding levels (RU) for human OSM, competing mAb or gp130-Fc were recorded. A rise in binding (RU) when a competing mAb or gp130-Fc was injected over an OSM surface indicates there is no competition with the immobilized test mAb and vice versa. Flow-cell (Fc1, etc.) immobilized mAbs appear along the horizontal sample rows of Table 10.

M2 was previously shown to compete with the commercial antibody MAB295 which is known not to compete with gp130 binding to OSM. The results demonstrate of the competition binding assays showed that M54, M55, M64, M69 and M71 compete with human gp130-Fc for OSM antigen (Table 11).

TABLE 11

Human gp130 Competition Matured Candidate Lead mAbs.

| | Binding Level (RU) | | | | Competition | | | |
|---|---|---|---|---|---|---|---|---|
| Sample | M2 (Fc1) | M54 (Fc2) | M69 (Fc3) | M71 (Fc4) | M2 (Fc1) | M54 (Fc2) | M69 (Fc3) | M71 (Fc4) |
| Buffer | −57 | 31 | 35 | 51 | | | | |
| Human gp130-Fc | 319 | 17 | 20 | 29 | No | Yes | Yes | Yes |
| MAB295 | −83 | 2903 | 2390 | 1989 | Yes | No | No | No |
| M6 | 985 | 11 | 16 | 19 | No | Yes | Yes | Yes |
| M54 | 1765 | 14 | 21 | 33 | No | Yes | Yes | Yes |
| M55 | 1417 | 14 | 21 | 35 | No | Yes | Yes | Yes |
| M64 | 1758 | 12 | 20 | 36 | No | Yes | Yes | Yes |
| M69 | 1243 | 13 | 17 | 21 | No | Yes | Yes | Yes |
| M71 | 1194 | −1 | 23 | 32 | No | Yes | Yes | Yes |

TABLE 11-continued

Human gp130 Competition Matured Candidate Lead mAbs.

| M2 | −73 | 3246 | 2483 | 2055 | Yes | No | No | No |
|---|---|---|---|---|---|---|---|---|
| Human gp130-Fc | 310 | 19 | 25 | 34 | No | Yes | Yes | Yes |
| Buffer | −52 | 35 | 37 | 55 | | | | |

| | Binding Level (RU) | | | Competition | | |
|---|---|---|---|---|---|---|
| Sample | M2 (Fc1) | M55 (Fc2) | M64 (Fc3) | M2 (Fc1) | M55 (Fc2) | M64 (Fc3) |
| Buffer | −54 | 50 | 30 | | | |
| Human gp130-Fc | 251 | 25 | 18 | No | Yes | Yes |
| MAB295 | −80 | 2950 | 1948 | Yes | No | No |
| M6 | 926 | 36 | 33 | No | Yes | Yes |
| M54 | 1634 | 19 | 16 | No | Yes | Yes |
| M55 | 1316 | 21 | 19 | No | Yes | Yes |
| M64 | 1665 | 20 | 22 | No | Yes | Yes |
| M69 | 1148 | 17 | 11 | No | Yes | Yes |
| M71 | 1127 | 22 | 17 | No | Yes | Yes |
| M2 | −74 | 3474 | 2203 | Yes | No | No |
| Human gp130-Fc | 248 | 26 | 20 | No | Yes | Yes |
| Buffer | −47 | 60 | 38 | | | |

Ability to Block pSTAT3 in A375 Cells

The calculated EC50 values for pSTAT3 inhibition performed in A375 cells in the presence or absence of 5 ng/ml hOSM for M6 and M9 and in-line matured variants of these Mabs, are shown in Table 12.

TABLE 12 pSTAT3 inhibition

| mAb ID | EC50 (ng/ml) | 95% Confidence Intervals | Curve Fit $R^2$ |
|---|---|---|---|
| M65 | 29.5 | 24.35 to 35.82 | 0.9921 |
| M67 | 37.7 | 30.93 to 45.92 | 0.9905 |
| M45 | 50.0 | 42.45 to 58.91 | 0.9931 |
| M83 | 71.2 | 59.59 to 85.05 | 0.9908 |
| MAB295 | 72.1 | 46.91 to 110.7 | 0.9848 |
| M54 | 78.5 | 66.11 to 93.23 | 0.9930 |
| M63 | 88.2 | 58.55 to 132.9 | 0.9819 |
| M64 | 97.1 | 77.01 to 122.4 | 0.9902 |
| M68 | 126.9 | 107.2 to 150.1 | 0.9924 |
| M69 | 141.7 | 115.1 to 174.5 | 0.9914 |
| M66 | 152.7 | 111.1 to 209.8 | 0.9833 |
| M71 | 159.6 | 128.3 to 198.5 | 0.9885 |
| M55 | 181.6 | 153.0 to 215.6 | 0.9869 |
| M42 | 191.3 | 93.67 to 390.7 | 0.9607 |
| M62 | 233.5 | 206.4 to 264.1 | 0.9947 |
| M53 | 236.6 | 196.3 to 285.2 | 0.9859 |
| M6 | 650.3 | 241.7 to 1750 | 0.9540 |
| M9 | 1218.0 | 352.8 to 4208 | 0.9614 |
| M85 | — | | 0.4454 |
| IL13 | — | | 0.3438 |

EXAMPLE 5. BIOLOGIC ACTIVITY

Macrophage-Chondrocyte Co-Culture Assay

M71 was evaluated in a macrophage-chondrocyte co-culture system. Differentiated macrophages are known to produce Oncostatin M (Hasegawa et al. *Rheumatology* 38:612-617, 1999). OSM can decrease the synthesis of the highly-sulfated proteoglycan aggrecan (GAG) that makes up a significant portion of the cartilage matrix.

The anti-human Oncostatin M antibodies were discovered using recombinant HEK-generated His-Avi tagged human and cynomolgous monkey Oncostatin M and the activity of these antibodies was evaluated using these molecules as well as bacterial-derived recombinant human Oncostatin M from R&D Systems (295-OM). None of these are identical to native endogenous human Oncostatin M, either because of the his-avi tag (HEK-generated Osm) or the lack of glycosylation (bacterial recombinant Osm). Macrophages are known to secrete Oncostatin M (Grove et al., J Lipid Res 32:1889-97, 1991) and oncostatin M decreases proteoglycan synthesis in human chondrocytes (Sanchez et al. OA and Cart. 12:810-10, 2004). Thus, a macrophage-chondrocyte co-culture system was used to determine the ability of the anti-human Oncostatin M antibodies to neutralize endogenous, or native, human Oncostatin M. Briefly, single alginate beads containing 40,000 normal human articular chondrocytes were cultured for 72 hours in the presence of differentiated human macrophages. These experiments were conducted in the presence of a dose-range of anti-Oncostatin M antibody. At the end of the experiment, proteoglycan synthesis was measured by the incorporation of radioactive $^{35}SO_4$.

CD14+ peripheral blood monocytes were obtained from AllCells. The monocytes were cultured on 48-well plates at 2.5×105 cells/well in 0.5 mls of macrophage medium (RPMI+Glutamine with 10% heat inactivated FBS, 1% NEAA and 1% Pen-Strep). The cells were treated with 100 ng/ml of macrophage-colony stimulating factor (M-CSF). After 48 hours the media was replaced to remove non-adherent cells. On day 6, the M-CSF containing macrophage medium was replaced with macrophage medium without M-CSF. On Day 8, the macrophage medium was replaced with chondrocyte medium (50% Ham's F-12/50% DMEM with 10% fetal calf serum) and a single alginate bead chondrocyte culture (Articular Engineering #CDD-H-2200) was added to each well. The aliquots of conditioned macrophage medium were reserved and stored at −80° C. for analysis of Oncostatin M levels using the R&D Systems Human Oncostatin M DuoSet (DY295).

The alginate bead-macrophage co-cultures were maintained in the presence of either 20 µg/ml of anti-human Oncostatin M antibodies (M64, M71, M55, M69) or in the presence of a dose-range (5 µg/ml to 0.00076 µg/ml; 1 to 3 dilutions) of antibody (M71 and M55). In addition, human IgG1 isotype control (CNT06234) was included on the plate at the highest concentration of anti-oncostatin M antibody tested. Other controls were chondrocytes only (no co-culture) and chondrocytes in the presence of 2 ng/ml human Oncostatin M. In addition, wells containing macrophages only were maintained in order to measure Oncostatin M production. After 72 hours of co-culture, 10 µCi/ml radioactive 35SO4 (Perkin-Elmer NEX041H002MC) was added to each well for an additional 20 hours.

Incorporation of $^{35}SO_4$ was measured using the CPC precipitation technique (MP BIomedicals (#190177). After 20 hours of incubation with $^{35}SO_4$, the labeled media was removed and each bead was washed twice with DPBS with Ca and Mg. After the second wash, 200 µl of citrate buffer (150 mM NaCl, 55 mM NaCitrate, ph 6.8) was added to each bead. The plates were incubated for 10 to 15 min at 37° C. until the beads were dissolved. A 100 µl aliquot from each well was transferred to a Millipore Multiscreen 96-well filter plate prewetted with 1% CPC and then 10 µl of 10% CPC was added to each well for 5 minutes. Vacuum was then applied to the plate until the filters were dry. Each well was then washed 2 times with 200 µl of 1% CPC and vacuum was applied each time until the filters were dry. The plastic bottom was then removed from the plate and replaced with a sealer (Perkin Elmer #6005185). Scintillation fluid (50 µl, Perkin Elmer #6013621) was added to each well and a plate sealer was applied to the top of the plate. The plate was then counted on a Top Count reader.

Figure 3:
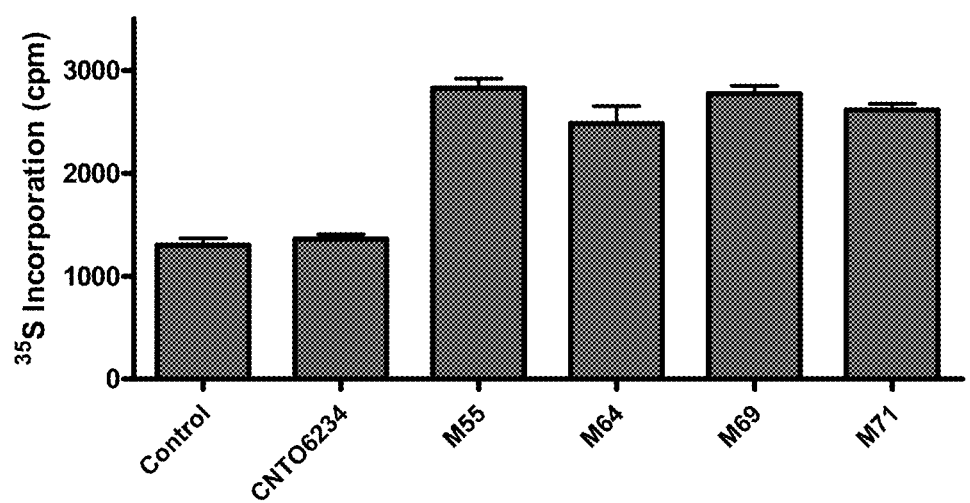
FIG. 3 is a column graph showing the effect of M64, M71, M55, and M69 at 20 μg/ml in increasing $^{35}SO_4$-uptake, a measure of increased proteoglycan synthesis, above the level observed in the absence of antibody and where the non-specific isotype antibody was a control in co-cultures of human chondrocytes in alginate beads and human macrophages capable of secreting OSM.

At 20 µg/ml, M64, M71, M55, and M69 increased proteoglycan synthesis above the level observed in the absence of antibody while the isotype control had no effect (FIG. 3). In a separate experiment, M71 dose-dependently increased proteoglycan synthesis to the level exhibited by chondrocytes alone (defined as 100% neutralization), with an EC50 of 30 ng/ml and the isotype control had no effect. These data demonstrate that macrophage-derived Osm decreases proteoglycan synthesis in the co-cultured chondrocytes and that the anti-human Oncostatin M antibodies neutralize native Oncostatin M.

Human Lung Fibroblast Phospho-STAT3 Assay

OSM induces proliferation and collagen production in normal human lung fibroblasts (Scaffidi et al., Br. J. Pharmacol 136: 793-801, 2002). Over-production of collagen by fibroblasts is a key feature of a number of pathological conditions (Lim et al. Oncogene 23(39): 5416-25, 2006; Huang et al. J Cell Biochem 81(1): 102-13, 2001). Oncostatin M receptor signaling activates the JAK-STAT pathway and phosphorylation of STAT3 is an early event in the signaling pathway (Auguste et al. (1997) Signaling of Type II Oncostatin M Receptor. J Biol Chem 272:15760-15764). The ability of Oncostatin M to generate pSTAT3 was determined in normal human lung fibroblasts (NHLF) using the R&D Systems human/mouse pSTAT3 Duoset (DYC4607-5). This assay was then used to determine the ability of M55 and M71 to neutralize Oncostatin M signaling.

These experiments were carried out using NHLF from Lonza (CC-2512) grown in Lonza proprietary FGM-2 (CC-3132) media. Briefly, the cells were plated at 25,000 cells/well in FGM-2 and cultured for 24 hours. The cells were then treated with Oncostatin M or antibody plus Oncostatin M for 10 minutes. In order to avoid temperature dependent effects during this 10 minute incubation, all of the solutions used to prepare the treatments were pre-warmed and maintained at 37° C. After the 10 minute treatment, media was aspirated away and replaced with complete lysis buffer. The lysis buffer (pH=7.2) consisted of 1% NP-40, 1% sodium deoxycholate, 0.1% SDS, 0.15M NaCl and 0.01M sodium phosphate and was stored at 4° C. At the time of use, complete lysis buffer was prepared by adding 1 tablet of Protease Inhibitor Cocktail (Roche, 11836153001) and 110 µL HALT phosphatase inhibitor (Thermo Scientific 78420) to 11 mls of lysis buffer. After the 10 minute lysis step, the resulting lysate was ready for pSTAT3 detection.

To determine the Oncostatin M dose-response, NHLF cells were treated with a dose-range of OSM (100 ng/ml to 0.024 ng/ml w/1 to 4 dilutions, triplicate wells). A dilution plate was prepared in pre-warmed PBS+1% BSA in which the concentration of Osm in each well was 10× higher than the final concentration needed for treatment, with media-only wells included as untreated controls. The media was completely removed from the culture plate and replaced with 180 µl of pre-warmed FGM-2. A timer was started for 10 minutes and then 20 µl was transferred from each well in the dilution plate to the corresponding well in the culture plate. After 10 minutes, the treatment solutions in the cell plate were completely removed by aspiration and replaced with 100 µl of complete lysis buffer. To minimize differences in incubation time, the lysis buffer was added to wells in the same order as the treatments. The assay plate was then placed on a shaker for 10 minutes. After shaking, the lysates were either frozen at −80° C. for later testing or transferred directly to an ELISA plate coated with anti-pSTAT3. The ELISA (R&D Systems human/mouse pSTAT3 Duoset) was carried out according to the manufacturer's instructions with the exceptions that 1) only 90 µl of lysate or standard was added to each well and 2) SuperSignal Pico (ThermoScientific 37069) was used as the HRP substrate. The ELISA plate was read for luminescence on a Victor3 plate reader.

To evaluate the ability of the M55 and M71 to neutralize OSM signaling in NHLFs, the cells were treated with a dose-range of anti-OSM antibody (triplicate wells, 500 ng/ml to 0.005 ng/ml with 1-10 dilutions or 50 ng/ml to 1.563 ng/ml with 1 to 2 dilutions) in the presence of 2 ng/ml human Osm. A dilution plate was prepared in PBS for the antibody dose-response treatment at 20× the final concentration, with wells included for the isotype control (at the highest concentration of the anti-OSM antibody) as well as with no antibody for both the untreated control and the cells treated only with OSM. Human oncostatin M was prepared separately at 40 ng/ml (20× the final concentration) in FGM-2. The 20× antibody and OSM solutions were mixed in equal volumes in the dilution plate to generate 10× treatment solutions and the plate was incubated for 1 hour at 37° C. to allow OSM to bind to the antibody. After 1 hour, the media was removed from the culture plate and replaced with 180 µl of pre-warmed FGM-2. A timer was started for 10 minutes and 20 µl was transferred from each well in the dilution plate to the corresponding well in the culture plate. After 10 minutes, the solutions in the cell plate were completely removed by aspiration and replaced with 100 µl of complete lysis buffer. To minimize differences in incubation time, the lysis buffer was added to wells in the same order as the treatments. The assay plate was then placed on a shaker for 10 minutes. After shaking, the lysates were either frozen at −80° C. for later testing or transferred directly to an ELISA plate coated with anti-pSTAT3. The ELISA (R&D Systems human/mouse pSTAT3 Duoset) was carried out according to the manufacturer's instructions with the exceptions that 1) only 90 pl of lysate or standard was added to each well and 2) SuperSignal Pico (ThermoScientific 37069) was used as the HRP substrate. The ELISA plate was read for luminescence on a Victor3 plate reader.

Figure 4A:
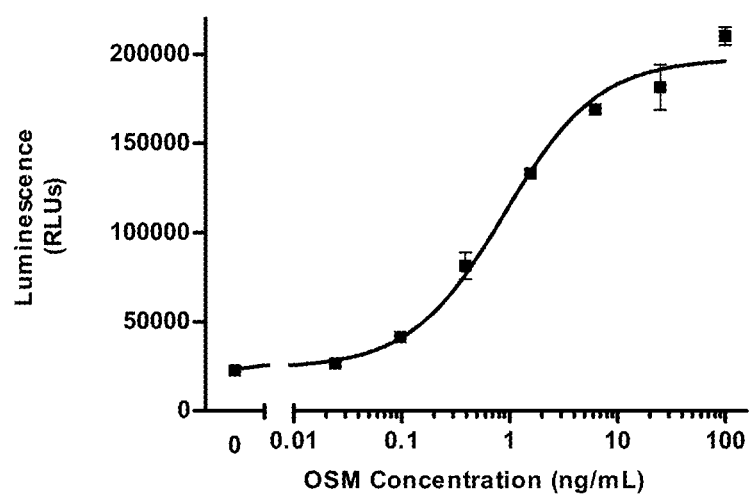
FIG. 4A is a graph in showing the dose response of human OSM stimulated pSTAT3 in NHLF cells where the EC50 was found to be approximately 1 ng/ml.
Figure 4B:
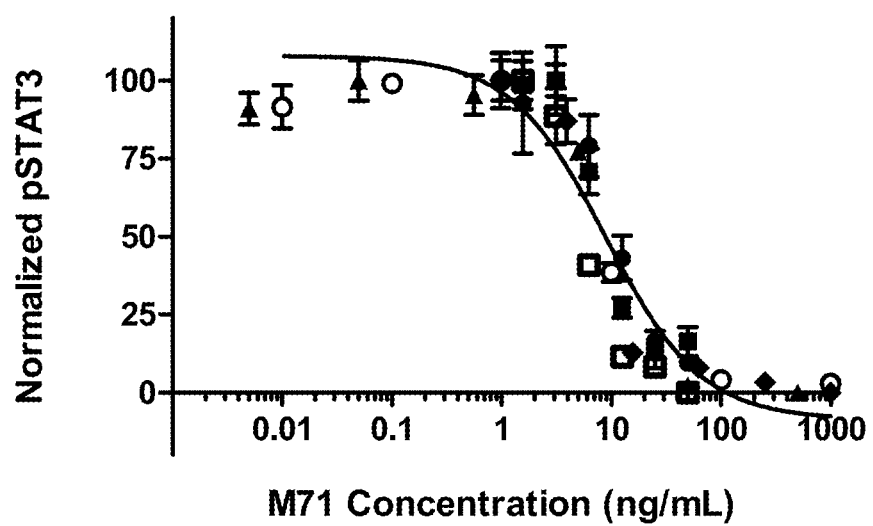
FIG. 4B is a graph showing the ability of the antibody M71 to neutralize the pSTAT3 signal in the presence of 2 ng/ml OSM.

Human Oncostatin M increased pSTAT3 in NHLF cells with an EC50 of approximately 1 ng/ml. An example of an Oncostatin M dose response is provided in FIG. 4A. For this example, the EC50 was 0.90 ng/ml with a 95% confidence interval from 0.70 to 1.17 ng/ml. The ability of the anti-oncostatin M antibodies to neutralize was determined in the presence of 2 ng/ml of Oncostatin M and all of the data were normalized to the luminescence in the presence of 2 ng/ml OSM with no antibody present. FIG. 4B shows the dose-dependent neutralization of OSM-induced STAT3 phosphorylation by M71. As the concentration of M71 is increased, the extent of STAT3 phosphorylation decreases. The dose-response curve was calculated from data from six separate experiments and the calculated IC50 for M71 was 8.9 ng/ml with a 95% confidence interval from 6.9 to 11.6 ng/ml.

EXAMPLE 6: IN VIVO ACTIVITY

M71 was evaluated for its ability to block the production of cytokines in vivo after systemic administration human Oncostatin M. Intraperitoneal injection of human Oncostatin M increases levels of certain serum cytokines, presumably through and interaction with the murine leukemia inhibitory factor receptor.

Systemic (i.p.) administration of human oncostastin M to mice was developed as a model to evaluate the ability of the anti-oncostatin M monoclonal antibodies to neutralize in an in vivo setting. Mice were injected i.p. with 10 µg of human Oncostatin M in 200 µl of PBS or PBS vehicle control. After 1 hour the mice were anesthetized with CO2 and blood was collected by terminal cardiac puncture. The individual blood samples were allowed to clot on ice for 20 min and then spun at 3500 rpm for 10-15 minutes. Serum samples were kept frozen until analyzed, as per the manufacturer's instructions, with the Milliplex Murine MAP Cytokine/Chemokine Multiplex (32) Panel. Analysis of the samples demonstrated that, compared to vehicle control, human Oncostatin M significantly increased serum levels of murine KC, IP-10, MCP-1, IL-6 and eotaxin, with no effect on the other cytokines in the panel. These data demonstrate that injection of human Oncostatin M induces cytokine release, presumably through an interaction with the murine leukemia inhibitory factor receptor (Richards et al. J Immunol. 159:2431-37, 1997; Lindberg et al., Mol Cell Biol 18:3357-3367, 1988) that can be used to test the ability of the anti-Oncostatin M antibodies to neutralize in vivo.

M71 and M55 were evaluated in the mouse systemic administration model. Briefly, mice were dosed subcutaneously with M71 or M55 (human IgG1 anti-human Osm at 20, 2.0 or 0.2 mg/kg), CNT06234 (huIgG1 isotype control, 20 mg/kg) or PBS in a volume of 10 µl/g. After 24 hours, each mouse was then injected i.p. with either 10 µg of in-house generated CHO cell-derived recombinant human oncostatin M in PBS (Sigma D8357) w/0.1% mouse serum albumin (Sigma A3559) or with PBS-MSA vehicle control alone (200 pt total volume). After 1 hour the mice were anesthetized with CO2 and blood was collected by terminal cardiac puncture. The individual blood samples were allowed to clot on ice for 20 min and then spun at 3500 rpm for 10-15 minutes. Serum samples were kept frozen until analyzed using the Milliplex Murine MAP Cytokine/Chemokine Multiplex (32) Panel. Serum samples were analyzed as per the manufacturer's instructions.

Figure 5A:
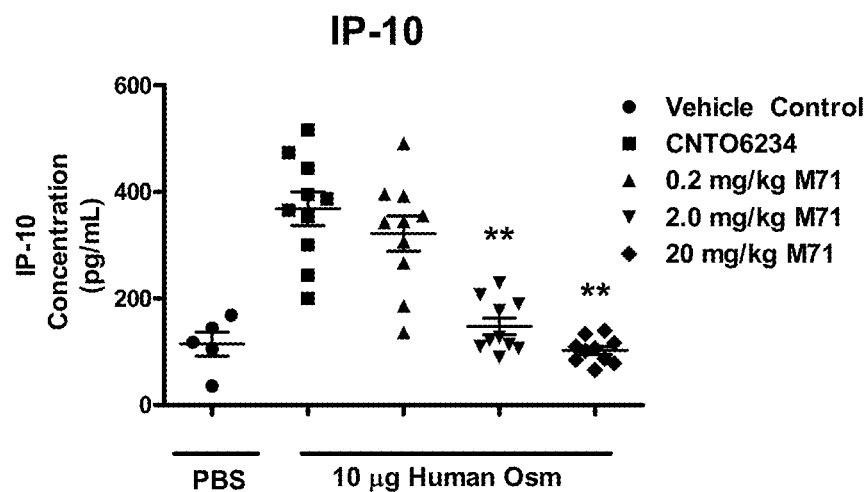
FIGS. 5A and B are scatter plots showing the amount of IP-10 (A) and MCP-1 (B) detected in the serum of individual mice after challenge with OSM and with or without pretreatment with the indicated concentration of M71 antibody.

Human oncostatin M induced significant (unpaired Student's t-test) increases in the serum levels of five of the cytokines detected by the kit: eotaxin, IL-6, IP-10, KC and MCP-1. Pre-dosing with the isotype control CNT06234 at 20 mg/kg had no effect on oncostatin M-induced cytokine release. However, pre-dosing with M71 significantly reduced serum levels of IP-10, MCP-1, IL-6 and eotaxin at 2.0 and 20 mg/kg and KC at 20 mg/kg. There was no effect on any of the cytokines at 0.2 mg/kg of M71. The effect of M71 and the isotype control on IP-10 and MCP-1 are shown in FIGS. 5A and B, respectively. Less robust neutralization was observed with M55 as neutralization at both 20 and 2.0 mg/kg was seen only with IP-10. Serum levels of IL-6, eotaxin and MCP-1 were reduced at 20 mg/kg M55 but no reduction in KC levels were seen at any dose of M55. These data demonstrate the ability of the anti-Oncostatin M antibodies to neutralize the biological effects of exogenous human oncostatin M in the murine systemic administration model.

IP-10, interferon gamma-induced protein 10 kDa or small-inducible cytokine B10, is a protein that in humans is encoded by the CXCL10 gene (C-X-C motif chemokine 10 (CXCL10). CXCL10 has been attributed to several roles, such as chemoattraction for monocytes/macrophages, T cells, NK cells, and dendritic cells, and promotion of T cell adhesion to endothelial cells. KC, now known as chemokine (C-X-C motif) ligand 1 (CXCL1), is a small cytokine belonging to the CXC chemokine family that was previously called GRO1 oncogene, GROα, Neutrophil-activating protein 3 (NAP-3) and melanoma growth stimulating activity, alpha (MSGA-α). In humans, this protein is encoded by the CXCL1 gene. CXCL1 is expressed by macrophages, neutrophils and epithelial cells, and has neutrophil chemoattractant activity.

EXAMPLE 7. CO-CRYSTALLOGRAPHY

A Fab fragment comprising the V-regions H17 (SEQ ID NO: 51) and L180 (SEQ ID NO: 55) was crystallized with human OSM (SEQ ID NO: 10) residues 26-212.

OSM shares its four-helix bundle three-dimensional structure with other members of the gp130 cytokine family. The four-helix bundle architecture is characterized by four a helical segments designated A (residues 10-37), B (residues 67-90), C (residues 105-131) and D (residues 159-185) linked by relatively unstructured loops. OSM interacts with gp130 via an epitope termed Site II which includes amino acid residues (Q16, Q20, G120, N123, N124) located in helices A and C (Deller et al. *Structure* 8(8): 863-874, 2000; Liu et al. *Int. J. Mol. Med.* 23: 161-172, 2009). Site III, the epitope responsible for OSM interaction with OSMRβ and LIFRα, is believed to be largely defined by residues located in helix D (Deller et al. Structure 8(8): 863-874, 2000).

Crystallization

Crystallization of the complex was performed by the sitting-drop vapor-diffusion method at 20° C. using the Oryx4 protein crystallization robot (Douglas Instruments), dispensing equal volumes of 0.2 µL protein complex (10.95 mg/mL) and 0.2 µL reservoir solution. Multiple crystallization screens were performed. The majority of droplets remained clear, reflecting the high solubility of the complex. Crystals were obtained from 0.1 M MES pH 6.5, 2.4 M ammonium sulfate and 0.1 M Tris pH 8.5, 3.5 M sodium formate.

Result of Crystal Structure Solution

Figure 5B:
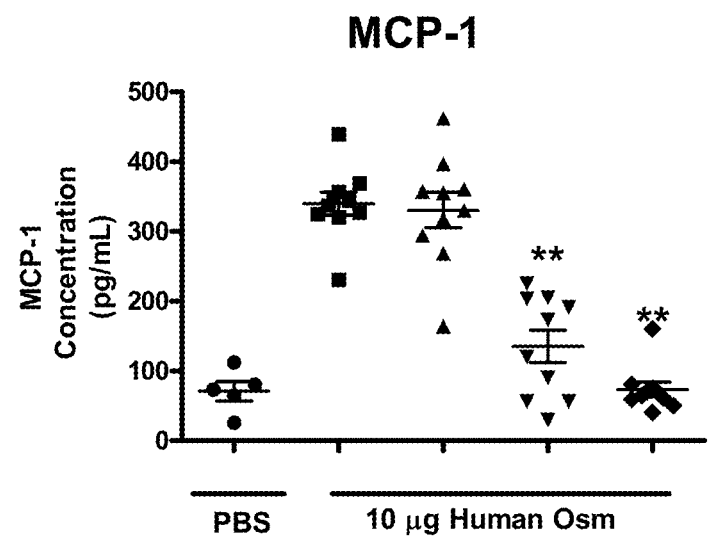

The OSM residues in contact with H14/L180 Fab constitute the binding epitope. The antibody residues in contact with OSM constitute the binding paratope. All six CDRs of the two variable domains are involved in OSM binding. Residues in contact are given in Table 13 and shown in FIG. 5. The long CDR-L1, together with the CDRs of the heavy chain variable region H1, form a valley-like antigen binding site with a small ridge at the bottom (FIG. 4C, left panel). Upon binding, the two sides of the valley embrace the OSM four-helix bundle along helices A and C with the bottom ridge binding in between the two helices (FIG. 4C, right panel). The antibody and antigen binding interface buries 2,514 Å 2 of solvent accessible surface (1225 Å 2 for Ab and 1298 Å 2 for Ag). Although there are a number of charges residues at the interface, there is no charge-charge pairing, suggesting vdw and H-bonding play the most important roles in antibody and antigen interactions.

TABLE 13

| OSM | VH (H17) | VL (L180) |
|---|---|---|
| Q16 | Y32, R98 | |
| K19 | Y105 | Y55, E61 |
| Q20 | S31, P100, V101 | |
| D22 | | I36 |
| L23 | P100, V101, A104, Y105 | Y97 |
| Q25 | | S34 |
| D26 | | G31, S32, S33 |
| T27 | | S32, S33 |
| S28 | | S32, F38, F98 |
| R29 | | F38, Y97, F98 |
| D32 | | S32 |
| I105 | R59 | |
| E106 | | T100 |

TABLE 13-continued

| OSM | VH (H17) | VL (L180) |
|---|---|---|
| E109 | Y57, R59 | |
| K110 | | F98, S99 |
| Q112 | Y57 | |
| M113 | Y57, R59, S102 | T100 |
| P116 | W33, Y52 | |
| N117 | W33, V101, S102 | |
| L119 | Y52, D55 | |
| G120 | T30, Y52 | |

\* The distance cutoffs are 3.3 Å for H bonds (highlighted in bold) and 3.9 Å for vdw contacts.

The H17/L180 Fab thus contacts OSM at residues previously shown to be contacted by gp130; Q20 and G120, and along the A and C helices.

EXAMPLE 8: PHARMACOKINETICS

OSM is a soluble target associated with the inflammatory processes as opposed to a cell-surface displayed target on a cell. The nature of a complete IgG comprising the binding regions as discovered herein and additionally having an Fc domain can thus be tailored to the purpose and therapeutic specification related to its use using methods of engineering the Fc with mutations conferring altered FcR binding.

In the present composition, a sustained activity and persistence in the circulation is a beneficial specification of a therapeutic monoclonal IgG. Therefore, an Fc-domain having enhanced affinity for the neonatal receptor (FcRn).

Using mutations previously described, M428L (MedImmune U.S. Pat. No. 7,670,600), in combination with N434S (U.S. Pat. No. 7,371,826, WO2006/053301), a mutated and a wild-type antibody were constructed using standard recombinant techniques. These two Mabs, M71 and M71 L/S were compared in standard activity assays and compared for persistence in the circulation of a non-human primate.

Assays

M71 and M71 L/S were compared side-by-side in the A375-S2 proliferation assay. Dose-responses were evaluated from a starting concentration of 1 µg/ml, with 1 to 5 dilutions to 0.00032 µg/ml. At a concentration of 1 µg/ml the isotype controls for these antibodies, CNT03930 and CNT08852, respectively, had no effect on the ability of 2 ng/ml of human Oncostatin M to inhibit proliferation. Both M71 and M71 L/S completely neutralized the effect of Oncostatin M at 1 µg/ml, with no measurable difference in IC50.

M71 and M71 L/S were compared in the mouse systemic administration model. Briefly, mice were dosed subcutaneously with M71 and M71 L/S (20, 10 or 5.0 mg/kg), CNT03930 (huIgG1 isotype control, 20 mg/kg), CNT08852 (isotype control for Fc mutated version, 20 mg/kg) or PBS in a volume of 10 µl/g. After 24 hours, each mouse was injected i.p. with either 10 µg of in-house generated CHO cell-derived recombinant human oncostatin M in PBS (Sigma D8357) w/0.1% mouse serum albumin (Sigma A3559) or with PBS-MSA vehicle control alone (200 µL total volume). After 1 hour the mice were anesthetized with CO2 and blood was collected by terminal cardiac puncture. The individual blood samples were allowed to clot on ice for 20 min and then spun at 3500 rpm for 10-15 minutes. Serum samples were kept frozen until analyzed using a custom Millipore murine multiplex consisting of beads specific for IL-6, MCP-1, eotaxin, KC and IP-10. Neither isotype control had any effect on cytokine release induced by human oncostatin M. However, both M71 and M71 L/S neutralized oncostatin M-induced cytokine release, with no apparent differences in potency or efficacy.

Pharmacokinetic Analysis

The serum half-life of M71 and M71 L/S were compared in a non-terminal cynomolgus monkey pharmacokinetics study. The study included a total of 12 cynomolgus monkeys and evaluated subcutaneous (s.c., n=3) and intravenous (i.v., n=3) administration for each antibody. The antibodies were dosed at 3 mg/kg and the study was carried out over 60 days. Blood samples were taken at 1 (IV groups only) and 6 hours and on days 1, 2, 4, 6, 8, 12, 16, 30, 37, 45 and 60. Serum from the samples was frozen at −80° C. until testing. Antibody levels in the serum were determined using an ELISA optimized in cynomologous monkey serum for the MesoScale Discovery platform. The biotinylated capture antibody was an anti-idotype antibody raised against M71 (mouse anti-M71). The detection antibody was ruthenium-labeled anti-human IgG and the readout was MesoScale Discovery chemiluminescence.

Figure 6A:
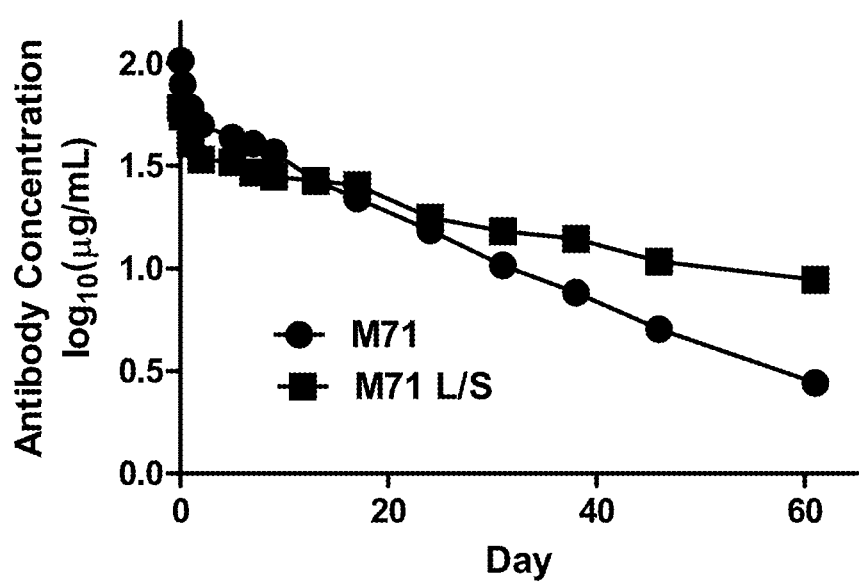
FIGS. 6A and B are graphs showing the serum concentration over time in cynomolgous monkeys after intravenious (A) or subcutaneous (B) administration of 3 mg/Kg M71 or an Fc variant of M71.
Figure 6B:
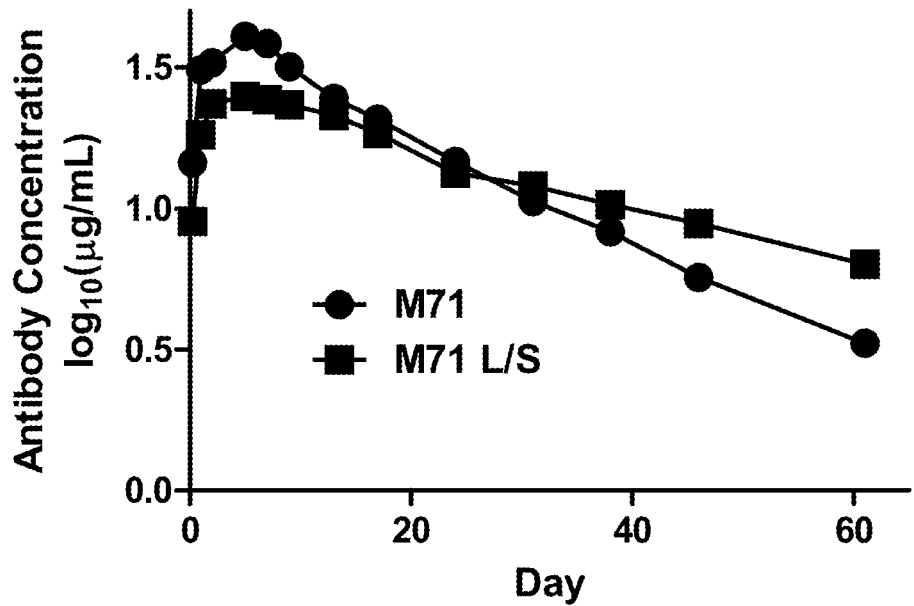

The results of the study are shown in FIGS. 6A and B. FIG. 6A shows the plots from the i.v. dosing where the serum half-life of M71 was 15.21+/−3.0 days and the half-life of M71 L/S was 29.4+/−2.3 days. Similar results were obtained from s.c. dosing (FIG. 6B) with a serum half-life of 15.4+/−4 days for M71 and 32.0+/−5.9 days for M71 L/S.

The results showed that M71 L/S t ½ increased about two-fold as compared to M71.

What is claimed:

1. A method of treating a human patient afflicted with idiopathic pulmonary fibrosis said method comprising administering to said patient a therapeutically effective amount of a composition of an antibody comprising a light chain variable region amino acid sequence of SEQ ID NO: 51 and a heavy chain variable region amino acid sequence of SEQ ID NO: 55, and a pharmaceutically acceptable excipient or carrier.

2. The method of claim 1, wherein the antibody comprises a constant region mutated to enhance the affinity of the antibody to the neonatal receptor (FcRn) as compared to an antibody with wild-type IgG1 constant domain sequence, the mutations being M428L and N434S, wherein the numbering is according to the Kabat EU numbering.

3. A method of treating a human patient afflicted with idiopathic pulmonary fibrosis, said method comprising administering to said patient a therapeutically effective amount of a composition of an antibody comprising an H-CDR1 amino acid sequence of SEQ ID NO: 14; an H-CDR2 amino acid sequence of SEQ ID NO: 17; an H-CDR3 amino acid sequence of SEQ ID NO: 21; an L-CDR1 amino acid sequence of SEQ ID NO: 38; an L-CDR2 amino acid sequence of SEQ ID NO: 43; and an L-CDR3 amino acid sequence of SEQ ID NO: 46.

4. The method of claim 3, wherein the antibody comprises an IgG1 constant region mutated to enhance the affinity of the antibody to the neonatal receptor (FcRn) as compared to an antibody with a wild-type IgG1 constant domain sequence and the mutations are M428L and N434S according to the Kabat EU numbering.

* * * * *

SEQUENCE LISTING

```
<160> NUMBER OF SEQ ID NOS: 63

<210> SEQ ID NO 1
<211> LENGTH: 98
<212> TYPE: PRT
<213> ORGANISM: Homo sapiens
<220> FEATURE:
<221> NAME/KEY: VARIANT
<222> LOCATION: (33)..(33)
<223> OTHER INFORMATION: X may be Ala or Gly
<220> FEATURE:
<221> NAME/KEY: VARIANT
<222> LOCATION: (50)..(50)
<223> OTHER INFORMATION: X may be Gly or Trp
<220> FEATURE:
<221> NAME/KEY: VARIANT
<222> LOCATION: (52)..(52)
```

```
<223> OTHER INFORMATION: X may be Ile or Ser
<220> FEATURE:
<221> NAME/KEY: VARIANT
<222> LOCATION: (53)..(53)
<223> OTHER INFORMATION: X may be Ala or Pro
<220> FEATURE:
<221> NAME/KEY: VARIANT
<222> LOCATION: (54)..(54)
<223> OTHER INFORMATION: X may be Ile or Tyr
<220> FEATURE:
<221> NAME/KEY: VARIANT
<222> LOCATION: (55)..(55)
<223> OTHER INFORMATION: X may be Asn or Phe

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Xaa Ile Ser Trp Val Arg Gln Ala Pro Gly Gln Gly Leu Glu Trp Met
        35                  40                  45

Gly Xaa Ile Xaa Xaa Xaa Xaa Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 2
<211> LENGTH: 98
<212> TYPE: PRT
<213> ORGANISM: Homo sapiens
<220> FEATURE:
<221> NAME/KEY: VARIANT
<222> LOCATION: (31)..(31)
<223> OTHER INFORMATION: X may be Asp, Asn, or Ser
<220> FEATURE:
<221> NAME/KEY: VARIANT
<222> LOCATION: (33)..(33)
<223> OTHER INFORMATION: X may be Asp, Gly, or Trp
<220> FEATURE:
<221> NAME/KEY: VARIANT
<222> LOCATION: (35)..(35)
<223> OTHER INFORMATION: X may be His or Ser
<220> FEATURE:
<221> NAME/KEY: VARIANT
<222> LOCATION: (50)..(50)
<223> OTHER INFORMATION: X may be Ala, Asn, Gly, or Val
<220> FEATURE:
<221> NAME/KEY: VARIANT
<222> LOCATION: (52)..(52)
<223> OTHER INFORMATION: X may be Asn, Lys, Ser, or Trp
<220> FEATURE:
<221> NAME/KEY: VARIANT
<222> LOCATION: (53)..(53)
<223> OTHER INFORMATION: X may be Gln, Gly, Ser, or Tyr
<220> FEATURE:
<221> NAME/KEY: VARIANT
<222> LOCATION: (54)..(54)
<223> OTHER INFORMATION: X may be Asp or Ser
<220> FEATURE:
<221> NAME/KEY: VARIANT
<222> LOCATION: (56)..(56)
<223> OTHER INFORMATION: X may be Gly or Ser

<400> SEQUENCE: 2

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Xaa Tyr
            20                  25                  30

Xaa Met Xaa Trp Val Arg Gln Ala Pro Gly Lys Gly Leu Glu Trp Val
        35                  40                  45

Ser Xaa Ile Xaa Xaa Xaa Gly Xaa Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 3
<211> LENGTH: 98
<212> TYPE: PRT
<213> ORGANISM: Homo sapiens
<220> FEATURE:
<221> NAME/KEY: VARIANT
<222> LOCATION: (31)..(31)
<223> OTHER INFORMATION: X may be Asn or Ser
<220> FEATURE:
<221> NAME/KEY: VARIANT
<222> LOCATION: (35)..(35)
<223> OTHER INFORMATION: X may be Gly or Ser
<220> FEATURE:
<221> NAME/KEY: VARIANT
<222> LOCATION: (50)..(50)
<223> OTHER INFORMATION: X may be Arg or Ile
<220> FEATURE:
<221> NAME/KEY: VARIANT
<222> LOCATION: (52)..(52)
<223> OTHER INFORMATION: X may be Asp or Tyr
<220> FEATURE:
<221> NAME/KEY: VARIANT
<222> LOCATION: (54)..(54)
<223> OTHER INFORMATION: X may be Gly or Ser
<220> FEATURE:
<221> NAME/KEY: VARIANT
<222> LOCATION: (57)..(57)
<223> OTHER INFORMATION: X may be Asp or Tyr

<400> SEQUENCE: 3

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Xaa Tyr
            20                  25                  30

Trp Ile Xaa Trp Val Arg Gln Met Pro Gly Lys Gly Leu Glu Trp Met
        35                  40                  45

Gly Xaa Ile Xaa Pro Xaa Asp Ser Xaa Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg

<210> SEQ ID NO 4
<211> LENGTH: 11
<212> TYPE: PRT
<213> ORGANISM: Homo sapiens

<400> SEQUENCE: 4

Trp Gly Gln Gly Thr Leu Val Thr Val Ser Ser
1               5                   10
```

<210> SEQ ID NO 5
<211> LENGTH: 88
<212> TYPE: PRT
<213> ORGANISM: Homo sapiens
<220> FEATURE:
<221> NAME/KEY: VARIANT
<222> LOCATION: (30)..(30)
<223> OTHER INFORMATION: X may be Ala, Asp, Asn, Ser or Arg
<220> FEATURE:
<221> NAME/KEY: VARIANT
<222> LOCATION: (31)..(31)
<223> OTHER INFORMATION: X may be Asp, Gly, Lys, Asn, or Ser
<220> FEATURE:
<221> NAME/KEY: VARIANT
<222> LOCATION: (32)..(32)
<223> OTHER INFORMATION: X may be Ala, Asp, Phe, His, Asn, Ser Trp,
     Val or Tyr
<220> FEATURE:
<221> NAME/KEY: VARIANT
<222> LOCATION: (50)..(50)
<223> OTHER INFORMATION: X may be Ala, Asp, Phe, Gly, Asn, Lys, Thr or
     Tyr

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Xaa Xaa Xaa
            20                  25                  30

Leu Asn Trp Tyr Gln Gln Lys Pro Gly Lys Ala Pro Lys Leu Leu Ile
        35                  40                  45

Tyr Xaa Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys
                85

<210> SEQ ID NO 6
<211> LENGTH: 88
<212> TYPE: PRT
<213> ORGANISM: Homo sapiens
<220> FEATURE:
<221> NAME/KEY: VARIANT
<222> LOCATION: (30)..(30)
<223> OTHER INFORMATION: X may be Ala, Asn, Asp, Arg, or Ser
<220> FEATURE:
<221> NAME/KEY: VARIANT
<222> LOCATION: (31)..(31)
<223> OTHER INFORMATION: X may be Asn, Asp, Lys, or Ser
<220> FEATURE:
<221> NAME/KEY: VARIANT
<222> LOCATION: (32)..(32)
<223> OTHER INFORMATION: X may be Ala, Asn, Asp, His, Phe, Ser, Trp,
     or Tyr
<220> FEATURE:
<221> NAME/KEY: VARIANT
<222> LOCATION: (50)..(50)
<223> OTHER INFORMATION: X may be Ala, Asn, Asp, Gly, Lys, Phe, Thr, or
     Tyr

<400> SEQUENCE: 6

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Xaa Xaa Xaa
            20                  25                  30

Leu Ala Trp Tyr Gln Gln Lys Pro Gly Gln Ala Pro Arg Leu Leu Ile
        35                  40                  45

-continued

```
Tyr Xaa Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys
                 85
```

<210> SEQ ID NO 7
<211> LENGTH: 89
<212> TYPE: PRT
<213> ORGANISM: Homo sapiens
<220> FEATURE:
<221> NAME/KEY: VARIANT
<222> LOCATION: (30)..(30)
<223> OTHER INFORMATION: X may be Asn, Asp, Arg, Ser, or Thr
<220> FEATURE:
<221> NAME/KEY: VARIANT
<222> LOCATION: (31)..(31)
<223> OTHER INFORMATION: X may be Asn, Arg, or Ser
<220> FEATURE:
<221> NAME/KEY: VARIANT
<222> LOCATION: (32)..(32)
<223> OTHER INFORMATION: X may be Ala, Asp, Asn, Arg, His, or Ser
<220> FEATURE:
<221> NAME/KEY: VARIANT
<222> LOCATION: (33)..(33)
<223> OTHER INFORMATION: X may be Glu, Gln, His, Lys, Phe, Ser, or Tyr
<220> FEATURE:
<221> NAME/KEY: VARIANT
<222> LOCATION: (51)..(51)
<223> OTHER INFORMATION: X may be Ala, Asp, Gly or Ser

<400> SEQUENCE: 7

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Xaa Xaa Xaa
                 20                  25                  30

Xaa Leu Ala Trp Tyr Gln Gln Lys Pro Gly Gln Ala Pro Arg Leu Leu
         35                  40                  45

Ile Tyr Xaa Ala Ser Ser Arg Ala Thr Gly Ile Pro Asp Arg Phe Ser
         50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys
                 85
```

<210> SEQ ID NO 8
<211> LENGTH: 94
<212> TYPE: PRT
<213> ORGANISM: Homo sapiens
<220> FEATURE:
<221> NAME/KEY: VARIANT
<222> LOCATION: (31)..(31)
<223> OTHER INFORMATION: X may be Ala, His, Phe, Ser, or Tyr
<220> FEATURE:
<221> NAME/KEY: VARIANT
<222> LOCATION: (36)..(36)
<223> OTHER INFORMATION: X may be Asn, Glu, Lys, or Thr
<220> FEATURE:
<221> NAME/KEY: VARIANT
<222> LOCATION: (38)..(38)
<223> OTHER INFORMATION: X may be Ala, Asp, Asn, His, Phe, Ser, Trp, or Tyr
<220> FEATURE:
<221> NAME/KEY: VARIANT
<222> LOCATION: (56)..(56)
<223> OTHER INFORMATION: X may be Ala, Asp, Arg, Ser, Trp, or Tyr -continued

```
<400> SEQUENCE: 8

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Xaa Ser
            20                  25                  30

Ser Asn Asn Xaa Asn Xaa Leu Ala Trp Tyr Gln Gln Lys Pro Gly Gln
        35              40                  45

Pro Pro Lys Leu Leu Ile Tyr Xaa Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys
                85                  90

<210> SEQ ID NO 9
<211> LENGTH: 9
<212> TYPE: PRT
<213> ORGANISM: Homo sapiens
<220> FEATURE:
<221> NAME/KEY: VARIANT
<222> LOCATION: (3)..(3)
<223> OTHER INFORMATION: X may be Ala, Asp, Arg, Gly, His, Phe, Pro,
      Ser, or Tyr
<220> FEATURE:
<221> NAME/KEY: VARIANT
<222> LOCATION: (4)..(4)
<223> OTHER INFORMATION: X may be Asp, Asn, Arg, Glu, Gly, His, Ile,
      Leu, Lys, Phe, Ser, or Tyr
<220> FEATURE:
<221> NAME/KEY: VARIANT
<222> LOCATION: (5)..(5)
<223> OTHER INFORMATION: X may be Asp, Asn, Arg, Gly, His, Lys, Thr, or
      Ser
<220> FEATURE:
<221> NAME/KEY: VARIANT
<222> LOCATION: (6)..(6)
<223> OTHER INFORMATION: X may be Ala, Arg, Gly, Leu, Phe, Pro, Ser,
      Thr, Trp, or Val
<220> FEATURE:
<221> NAME/KEY: VARIANT
<222> LOCATION: (8)..(8)
<223> OTHER INFORMATION: X may be Asn, Arg, Ile, Leu, Phe, Trp, or Tyr

<400> SEQUENCE: 9

Gln Gln Xaa Xaa Xaa Xaa Pro Xaa Thr
1               5

<210> SEQ ID NO 10
<211> LENGTH: 10
<212> TYPE: PRT
<213> ORGANISM: Homo sapiens

<400> SEQUENCE: 10

Phe Gly Gln Gly Thr Lys Val Glu Ile Lys
1               5                   10

<210> SEQ ID NO 11
<211> LENGTH: 227
<212> TYPE: PRT
<213> ORGANISM: Homo sapiens

<400> SEQUENCE: 11

Ala Ala Ile Gly Ser Cys Ser Lys Glu Tyr Arg Val Leu Leu Gly Gln
1               5                   10                  15

Leu Gln Lys Gln Thr Asp Leu Met Gln Asp Thr Ser Arg Leu Leu Asp
            20                  25                  30
```

```
Pro Tyr Ile Arg Ile Gln Gly Leu Asp Val Pro Lys Leu Arg Glu His
        35                  40                  45

Cys Arg Glu Arg Pro Gly Ala Phe Pro Ser Glu Thr Leu Arg Gly
 50                  55                  60

Leu Gly Arg Arg Gly Phe Leu Gln Thr Leu Asn Ala Thr Leu Gly Cys
 65                  70                  75                  80

Val Leu His Arg Leu Ala Asp Leu Glu Gln Arg Leu Pro Lys Ala Gln
                 85                  90                  95

Asp Leu Glu Arg Ser Gly Leu Asn Ile Glu Asp Leu Glu Lys Leu Gln
                100                 105                 110

Met Ala Arg Pro Asn Ile Leu Gly Leu Arg Asn Asn Ile Tyr Cys Met
                115                 120                 125

Ala Gln Leu Leu Asp Asn Ser Asp Thr Ala Glu Pro Thr Lys Ala Gly
        130                 135                 140

Arg Gly Ala Ser Gln Pro Pro Thr Pro Thr Pro Ala Ser Asp Ala Phe
145                 150                 155                 160

Gln Arg Lys Leu Glu Gly Cys Arg Phe Leu His Gly Tyr His Arg Phe
                165                 170                 175

Met His Ser Val Gly Arg Val Phe Ser Lys Trp Gly Glu Ser Pro Asn
                180                 185                 190

Arg Ser Arg Arg His Ser Pro His Gln Ala Leu Arg Lys Gly Val Arg
        195                 200                 205

Arg Thr Arg Pro Ser Arg Lys Gly Lys Arg Leu Met Thr Arg Gly Gln
210                 215                 220

Leu Pro Arg
225

<210> SEQ ID NO 12
<211> LENGTH: 227
<212> TYPE: PRT
<213> ORGANISM: Macaca fascicularis

<400> SEQUENCE: 12

Ala Ala Met Gly Ser Cys Ser Lys Glu Tyr Arg Met Leu Leu Gly Gln
 1               5                  10                  15

Leu Gln Lys Gln Thr Asp Leu Met Gln Asp Thr Ser Arg Leu Leu Asp
                20                  25                  30

Pro Tyr Ile Arg Ile Gln Gly Leu Asp Ile Pro Lys Leu Arg Glu His
        35                  40                  45

Cys Arg Glu Ser Pro Gly Ala Phe Pro Ser Glu Thr Leu Arg Gly
 50                  55                  60

Leu Gly Arg Arg Gly Phe Leu Gln Thr Leu Asn Ala Thr Leu Gly Arg
 65                  70                  75                  80

Val Leu His Arg Leu Ala Asp Leu Glu Gln His Leu Pro Lys Ala Gln
                 85                  90                  95

Asp Leu Glu Arg Ser Gly Leu Asn Ile Glu Asp Leu Glu Lys Leu Gln
                100                 105                 110

Met Ala Arg Pro Asn Val Leu Gly Leu Arg Asn Asn Ile Tyr Cys Met
                115                 120                 125

Ala Gln Leu Leu Asp Asn Ser Asp Met Thr Glu Pro Thr Lys Ala Gly
        130                 135                 140

Arg Gly Thr Pro Gln Pro Pro Thr Pro Thr Pro Thr Ser Asp Val Phe
145                 150                 155                 160

Gln Arg Lys Leu Glu Gly Cys Ser Phe Leu Arg Gly Tyr His Arg Phe
```

```
                    165                 170                 175
Met His Ser Val Gly Arg Val Phe Ser Lys Trp Gly Glu Ser Pro Asn
            180                 185                 190

Arg Ser Arg Arg His Ser Pro His Gln Ala Leu Arg Lys Gly Val Arg
        195                 200                 205

Arg Thr Arg Pro Ser Arg Lys Gly Asn Arg Leu Met Pro Arg Gly Gln
    210                 215                 220

Leu Pro Arg
225

<210> SEQ ID NO 13
<211> LENGTH: 5
<212> TYPE: PRT
<213> ORGANISM: Homo sapiens

<400> SEQUENCE: 13

Ser Tyr Ala Ile Ser
1               5

<210> SEQ ID NO 14
<211> LENGTH: 5
<212> TYPE: PRT
<213> ORGANISM: Homo sapiens

<400> SEQUENCE: 14

Ser Tyr Trp Ile Ser
1               5

<210> SEQ ID NO 15
<211> LENGTH: 5
<212> TYPE: PRT
<213> ORGANISM: Homo sapiens

<400> SEQUENCE: 15

Ser Tyr Trp Ile Gly
1               5

<210> SEQ ID NO 16
<211> LENGTH: 17
<212> TYPE: PRT
<213> ORGANISM: Homo sapiens

<400> SEQUENCE: 16

Gly Ile Ile Pro Ile Phe Gly Asn Ala Asn Tyr Ala Gln Lys Phe Gln
1               5                   10                  15

Gly

<210> SEQ ID NO 17
<211> LENGTH: 17
<212> TYPE: PRT
<213> ORGANISM: Homo sapiens

<400> SEQUENCE: 17

Ile Ile Tyr Pro Gly Asp Ser Tyr Thr Arg Tyr Ser Pro Ser Phe Gln
1               5                   10                  15

Gly

<210> SEQ ID NO 18
<211> LENGTH: 17
<212> TYPE: PRT
<213> ORGANISM: Homo sapiens
```

```
<400> SEQUENCE: 18

Ile Ile Tyr Pro Gly Asp Ser Asp Thr Arg Tyr Ser Pro Ser Phe Gln
1               5                   10                  15

Gly

<210> SEQ ID NO 19
<211> LENGTH: 9
<212> TYPE: PRT
<213> ORGANISM: Homo sapiens

<400> SEQUENCE: 19

Tyr Gly Ala Lys Gly Leu Leu Asp Tyr
1               5

<210> SEQ ID NO 20
<211> LENGTH: 10
<212> TYPE: PRT
<213> ORGANISM: Homo sapiens

<400> SEQUENCE: 20

Gly Ser Val Phe Glu Ala Tyr Phe Asp Tyr
1               5                   10

<210> SEQ ID NO 21
<211> LENGTH: 10
<212> TYPE: PRT
<213> ORGANISM: Homo sapiens

<400> SEQUENCE: 21

Val Pro Val Ser Pro Ala Tyr Leu Asp Tyr
1               5                   10

<210> SEQ ID NO 22
<211> LENGTH: 9
<212> TYPE: PRT
<213> ORGANISM: Homo sapiens

<400> SEQUENCE: 22

Gly Phe Gly Ala Ser Tyr Leu Asp Tyr
1               5

<210> SEQ ID NO 23
<211> LENGTH: 17
<212> TYPE: PRT
<213> ORGANISM: Homo sapiens

<400> SEQUENCE: 23

Lys Ser Ser Gln Ser Val Leu Tyr Ser Ser Asn Asn Lys Asn Tyr Leu
1               5                   10                  15

Ala

<210> SEQ ID NO 24
<211> LENGTH: 17
<212> TYPE: PRT
<213> ORGANISM: Homo sapiens

<400> SEQUENCE: 24

Lys Ser Ser Gln Ser Val Leu Ser Ser Asn Asn Glu Asn Trp Leu
1               5                   10                  15

Ala

<210> SEQ ID NO 25
```

```
<211> LENGTH: 17
<212> TYPE: PRT
<213> ORGANISM: Homo sapiens

<400> SEQUENCE: 25

Lys Ser Ser Gln Ser Val Leu Ala Ser Ser Asn Asn Asn Asn Phe Leu
1               5                   10                  15

Ala

<210> SEQ ID NO 26
<211> LENGTH: 7
<212> TYPE: PRT
<213> ORGANISM: Homo sapiens

<400> SEQUENCE: 26

Trp Ala Ser Thr Arg Glu Ser
1               5

<210> SEQ ID NO 27
<211> LENGTH: 8
<212> TYPE: PRT
<213> ORGANISM: Homo sapiens

<400> SEQUENCE: 27

Gln Gln Tyr Tyr Ser Thr Pro Leu
1               5

<210> SEQ ID NO 28
<211> LENGTH: 8
<212> TYPE: PRT
<213> ORGANISM: Homo sapiens

<400> SEQUENCE: 28

Gln Gln Ser Phe Ser Phe Pro Ile
1               5

<210> SEQ ID NO 29
<211> LENGTH: 9
<212> TYPE: PRT
<213> ORGANISM: Homo sapiens
<220> FEATURE:
<221> NAME/KEY: VARIANT
<222> LOCATION: (3)..(3)
<223> OTHER INFORMATION: X may be Ser or Tyr
<220> FEATURE:
<221> NAME/KEY: VARIANT
<222> LOCATION: (4)..(4)
<223> OTHER INFORMATION: X may be Phe or Tyr
<220> FEATURE:
<221> NAME/KEY: VARIANT
<222> LOCATION: (6)..(6)
<223> OTHER INFORMATION: X may be Phe or Thr

<400> SEQUENCE: 29

Gln Gln Xaa Xaa Ser Xaa Pro Leu Thr
1               5

<210> SEQ ID NO 30
<211> LENGTH: 17
<212> TYPE: PRT
<213> ORGANISM: Homo sapiens

<400> SEQUENCE: 30

Lys Ser Ser Gln Ser Val Leu Ser Ser Gly Asn Asn Gly Asn Tyr Leu
1               5                   10                  15

Ala
```

```
<210> SEQ ID NO 31
<211> LENGTH: 17
<212> TYPE: PRT
<213> ORGANISM: Homo sapiens

<400> SEQUENCE: 31

Lys Ser Ser Gln Ser Val Leu Ser Ser Gly Ser Asn His Asn Tyr Leu
1               5                   10                  15

Ala

<210> SEQ ID NO 32
<211> LENGTH: 17
<212> TYPE: PRT
<213> ORGANISM: Homo sapiens

<400> SEQUENCE: 32

Lys Ser Ser Gln Ser Val Leu Ser Ser Arg Gly Asn Asn Asn Tyr Leu
1               5                   10                  15

Ala

<210> SEQ ID NO 33
<211> LENGTH: 17
<212> TYPE: PRT
<213> ORGANISM: Homo sapiens

<400> SEQUENCE: 33

Lys Ser Ser Gln Ser Val Leu Gly Ser Trp Gly Asn Asp Asn Tyr Leu
1               5                   10                  15

Ala

<210> SEQ ID NO 34
<211> LENGTH: 17
<212> TYPE: PRT
<213> ORGANISM: Homo sapiens

<400> SEQUENCE: 34

Lys Ser Ser Gln Ser Val Leu Tyr Ser Gly Gly Asn Gly Asn Tyr Leu
1               5                   10                  15

Ala

<210> SEQ ID NO 35
<211> LENGTH: 17
<212> TYPE: PRT
<213> ORGANISM: Homo sapiens

<400> SEQUENCE: 35

Lys Ser Ser Gln Ser Val Leu Gly Ser Trp Gly Asn Gly His Tyr Leu
1               5                   10                  15

Ala

<210> SEQ ID NO 36
<211> LENGTH: 17
<212> TYPE: PRT
<213> ORGANISM: Homo sapiens

<400> SEQUENCE: 36

Lys Ser Ser Gln Ser Val Leu Ser Ser Asn Gly Asn His Asn Tyr Leu
1               5                   10                  15

Ala
```

<210> SEQ ID NO 37
<211> LENGTH: 17
<212> TYPE: PRT
<213> ORGANISM: Homo sapiens

<400> SEQUENCE: 37

Lys Ser Ser Gln Ser Val Leu Ser Ser Asp Gly Asn His Asn Tyr Leu
1               5                   10                  15

Ala

<210> SEQ ID NO 38
<211> LENGTH: 17
<212> TYPE: PRT
<213> ORGANISM: Homo sapiens

<400> SEQUENCE: 38

Lys Ser Ser Gln Ser Val Leu Gly Ser Ser Asn Ile Asn Phe Leu
1               5                   10                  15

Ala

<210> SEQ ID NO 39
<211> LENGTH: 17
<212> TYPE: PRT
<213> ORGANISM: Homo sapiens

<400> SEQUENCE: 39

Lys Ser Ser Gln Ser Val Leu Gly Ser Gly Asp Asn Arg Asn Tyr Leu
1               5                   10                  15

Ala

<210> SEQ ID NO 40
<211> LENGTH: 17
<212> TYPE: PRT
<213> ORGANISM: Homo sapiens

<400> SEQUENCE: 40

Lys Ser Ser Gln Ser Val Leu Gly Ser Gly Tyr Asn Arg Asn Tyr Leu
1               5                   10                  15

Ala

<210> SEQ ID NO 41
<211> LENGTH: 17
<212> TYPE: PRT
<213> ORGANISM: Homo sapiens

<400> SEQUENCE: 41

Lys Ser Ser Gln Ser Val Leu Gly Ser Trp His Asn Asp Asn Tyr Leu
1               5                   10                  15

Ala

<210> SEQ ID NO 42
<211> LENGTH: 7
<212> TYPE: PRT
<213> ORGANISM: Homo sapiens

<400> SEQUENCE: 42

Lys Ala Ser Thr Arg Glu Ser
1               5

<210> SEQ ID NO 43
<211> LENGTH: 7

```
<212> TYPE: PRT
<213> ORGANISM: Homo sapiens

<400> SEQUENCE: 43

Ser Ala Ser Thr Arg Glu Ser
1               5

<210> SEQ ID NO 44
<211> LENGTH: 7
<212> TYPE: PRT
<213> ORGANISM: Homo sapiens

<400> SEQUENCE: 44

Asn Ala Ser Thr Arg Glu Ser
1               5

<210> SEQ ID NO 45
<211> LENGTH: 9
<212> TYPE: PRT
<213> ORGANISM: Homo sapiens

<400> SEQUENCE: 45

Gln Gln Tyr Ser Thr Thr Pro Leu Thr
1               5

<210> SEQ ID NO 46
<211> LENGTH: 9
<212> TYPE: PRT
<213> ORGANISM: Homo sapiens

<400> SEQUENCE: 46

Gln Gln Tyr Phe Ser Thr Pro Ile Thr
1               5

<210> SEQ ID NO 47
<211> LENGTH: 9
<212> TYPE: PRT
<213> ORGANISM: Homo sapiens
<220> FEATURE:
<221> NAME/KEY: VARIANT
<222> LOCATION: (4)..(4)
<223> OTHER INFORMATION: X may be Phe or Tyr
<220> FEATURE:
<221> NAME/KEY: VARIANT
<222> LOCATION: (8)..(8)
<223> OTHER INFORMATION: X may be Ile or Leu

<400> SEQUENCE: 47

Gln Gln Tyr Xaa Ser Thr Pro Xaa Thr
1               5

<210> SEQ ID NO 48
<211> LENGTH: 96
<212> TYPE: PRT
<213> ORGANISM: Homo sapiens

<400> SEQUENCE: 48

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Ile Ile Tyr Pro Gly Asp Ser Tyr Thr Arg Tyr Ser Pro Ser Phe
    50                  55                  60
```

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

<210> SEQ ID NO 49
<211> LENGTH: 102
<212> TYPE: PRT
<213> ORGANISM: Homo sapiens

<400> SEQUENCE: 49

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Ser Ser
            20                  25                  30

Arg Gly Asn Asn Asn Tyr Leu Ala Trp Tyr Gln Gln Lys Pro Gly Gln
        35                  40                  45

Pro Pro Lys Leu Leu Ile Tyr Lys Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
            85                  90                  95

Tyr Tyr Ser Thr Pro Leu
            100

<210> SEQ ID NO 50
<211> LENGTH: 102
<212> TYPE: PRT
<213> ORGANISM: Homo sapiens

<400> SEQUENCE: 50

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Ser Ser
            20                  25                  30

Asp Gly Asn His Asn Tyr Leu Ala Trp Tyr Gln Gln Lys Pro Gly Gln
        35                  40                  45

Pro Pro Lys Leu Leu Ile Tyr Lys Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
            85                  90                  95

Tyr Tyr Ser Thr Pro Leu
            100

<210> SEQ ID NO 51
<211> LENGTH: 102
<212> TYPE: PRT
<213> ORGANISM: Homo sapiens

<400> SEQUENCE: 51

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Gly Ser
            20                  25                  30

```
Ser Ser Asn Ile Asn Phe Leu Ala Trp Tyr Gln Gln Lys Pro Gly Gln
            35                  40                  45

Pro Pro Lys Leu Leu Ile Tyr Ser Ala Ser Thr Arg Glu Ser Gly Val
 50                      55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Phe Ser Thr Pro Ile
            100

<210> SEQ ID NO 52
<211> LENGTH: 102
<212> TYPE: PRT
<213> ORGANISM: Homo sapiens

<400> SEQUENCE: 52

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Ser Ser
            20                  25                  30

Gly Gly Asn Trp Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                      55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Tyr Thr Thr Pro Leu
            100

<210> SEQ ID NO 53
<211> LENGTH: 102
<212> TYPE: PRT
<213> ORGANISM: Homo sapiens

<400> SEQUENCE: 53

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Ser Ser
            20                  25                  30

Gly Ser Asn Arg Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                      55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Tyr Ser Thr Pro Leu
            100

<210> SEQ ID NO 54
<211> LENGTH: 108
<212> TYPE: PRT
<213> ORGANISM: Homo sapiens
```

-continued

<400> SEQUENCE: 54

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Ile Ile Tyr Pro Gly Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Ser Val Phe Glu Ala Tyr Phe Asp Tyr
            100                 105

<210> SEQ ID NO 55
<211> LENGTH: 108
<212> TYPE: PRT
<213> ORGANISM: Homo sapiens

<400> SEQUENCE: 55

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Ile Ile Tyr Pro Gly Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Pro Val Ser Pro Ala Tyr Leu Asp Tyr
            100                 105

<210> SEQ ID NO 56
<211> LENGTH: 15
<212> TYPE: PRT
<213> ORGANISM: Artificial Sequence
<220> FEATURE:
<223> OTHER INFORMATION: Consensus sequence for enzymatic biotinylation

<400> SEQUENCE: 56

Gly Leu Asn Asp Ile Phe Glu Ala Gln Lys Ile Glu Trp His Glu
1               5                   10                  15

<210> SEQ ID NO 57
<211> LENGTH: 109
<212> TYPE: PRT
<213> ORGANISM: Homo sapiens

<400> SEQUENCE: 57

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

-continued

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Gln Gly Thr Leu Val Thr Val Ser Ser
            100                 105

<210> SEQ ID NO 58
<211> LENGTH: 109
<212> TYPE: PRT
<213> ORGANISM: Homo sapiens

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Gly Gln Gly Thr Leu Val Thr Val Ser Ser
            100                 105

<210> SEQ ID NO 59
<211> LENGTH: 109
<212> TYPE: PRT
<213> ORGANISM: Homo sapiens

<400> SEQUENCE: 59

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Gly Gln Gly Thr Leu Val Thr Val Ser Ser
            100                 105

<210> SEQ ID NO 60
<211> LENGTH: 108
<212> TYPE: PRT
<213> ORGANISM: Homo sapiens

<400> SEQUENCE: 60

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys
            100                 105

<210> SEQ ID NO 61
<211> LENGTH: 113
<212> TYPE: PRT
<213> ORGANISM: Homo sapiens

<400> SEQUENCE: 61

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gln Gly Thr Lys Val Glu Ile
            100                 105                 110

Lys

<210> SEQ ID NO 62
<211> LENGTH: 107
<212> TYPE: PRT
<213> ORGANISM: Homo sapiens

<400> SEQUENCE: 62

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

```
<210> SEQ ID NO 63
<211> LENGTH: 107
<212> TYPE: PRT
<213> ORGANISM: Homo sapiens

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105
```